US012685569B2

(12) United States Patent
Stokes et al.

(10) Patent No.: US 12,685,569 B2
(45) **Date of Patent: *Jul. 21, 2026**

(54) MINIMALLY INVASIVE PEDICLE SCREW EXTENSION SLEEVE SYSTEM

(71) Applicant: Genesys Spine, Austin, TX (US)

(72) Inventors: John Stokes, Austin, TX (US); David L. Greenwald, Austin, TX (US); Josh Kaufmann, Austin, TX (US); Greg Calbert, Lakeway, TX (US); Scott Bryant, Austin, TX (US); Landon Gilkey, Austin, TX (US); Brian Bergeron, Austin, TX (US)

(73) Assignee: Genesys Spine, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/888,272

(22) Filed: Sep. 18, 2024

(65) Prior Publication Data

US 2025/0009397 A1 Jan. 9, 2025

Related U.S. Application Data

(63) Continuation of application No. 17/895,099, filed on Aug. 25, 2022, now Pat. No. 12,096,965, which is a continuation of application No. 16/828,082, filed on Mar. 24, 2020, now Pat. No. 11,426,214, which is a continuation of application No. 15/981,445, filed on May 16, 2018, now Pat. No. 10,603,086, which is a (Continued)

(51) Int. Cl.
*A61B 17/70* (2006.01)

(52) U.S. Cl.
CPC ........ *A61B 17/708* (2013.01); *A61B 17/7085* (2013.01)

(58) Field of Classification Search
CPC .............. A61B 17/708; A61B 17/7083; A61B 17/7085; A61B 17/7086
USPC ......................................................... 606/279
See application file for complete search history.

(56) References Cited

U.S. PATENT DOCUMENTS 8,066,739 B2 11/2011 Jackson
9,414,862 B2 8/2016 Miller
(Continued)

OTHER PUBLICATIONS

International Searching Authority, "Notification of Transmittal of the International Search Report and the Written Opinion of the International Searching Authority," mailed May 1, 2014 in international application No. PCT/US2014/014661.

*Primary Examiner* — Eduardo C Robert
*Assistant Examiner* — Christina Negrellirodriguez
(74) *Attorney, Agent, or Firm* — Trop, Pruner & Hu, P.C.

(57) ABSTRACT

An embodiment includes a system comprising: a tulip including a slot to receive a linkage, first and second side walls that define a portion of the slot, and a ring that couples the first side wall to the second side wall; wherein the ring couples to the first side wall at a thinned first proximal fulcrum and to the second side wall at a thinned second proximal fulcrum and the ring pivots about the first and second proximal fulcrums when the ring is forced proximally; wherein the first side wall includes a first sidewall projection that projects past the first proximal fulcrum and the second side wall includes a second sidewall projection that projects past the second proximal fulcrum. Other embodiments are described herein.

20 Claims, 31 Drawing Sheets

Related U.S. Application Data continuation of application No. 14/765,402, filed as application No. PCT/US2014/014661 on Feb. 4, 2014, now Pat. No. 10,004,543.

(60) Provisional application No. 61/760,385, filed on Feb. 4, 2013.

(56) References Cited

U.S. PATENT DOCUMENTS

| | | | |
|---|---|---|---|
| 12,096,965 B2 * | 9/2024 | Stokes | A61B 17/7085 |
| 2006/0079909 A1 * | 4/2006 | Runco | A61B 17/7086 |
| | | | 606/99 |
| 2009/0228052 A1 | 9/2009 | Beardsley et al. | |
| 2011/0178560 A1 * | 7/2011 | Butler | A61B 17/8863 |
| | | | 606/86 A |
| 2011/0202095 A1 * | 8/2011 | Semler | A61B 17/8605 |
| | | | 606/305 |
| 2011/0301647 A1 | 12/2011 | Hua | |

* cited by examiner

202

221

220

222

210

241 ————          ———— 240

250 ———

407

408

402

403

406

410

MINIMALLY INVASIVE PEDICLE SCREW EXTENSION SLEEVE SYSTEM

CLAIM OF PRIORITY

This application is a continuation of U.S. patent application Ser. No. 17/895,099, filed Aug. 25, 2022, which is a continuation of U.S. patent application Ser. No. 16/828,082, filed Mar. 24, 2020, now U.S. Pat. No. 11,426,214, issued Aug. 30, 2022, which is a continuation of U.S. patent application Ser. No. 15/981,445, filed May 16, 2018, now U.S. Pat. No. 10,603,086, issued Mar. 31, 2020, which is a continuation of U.S. patent application Ser. No. 14/765,402, filed on Aug. 3, 2015, now U.S. Pat. No. 10,004,543, issued Jun. 26, 2018, which is a 371 National Stage Entry of International Application No. PCT/US2014/014661, filed on Feb. 4, 2014, and titled "Minimally Invasive Pedicle Screw Extension Sleeve System", which claims priority to U.S. Provisional Patent Application No. 61/760,385, filed on Feb. 4, 2013, and titled "Minimally Invasive Pedicle Screw". The content of each of the above applications is hereby incorporated by reference.

BACKGROUND

Spinal fixation devices can be used to provide, for example, immobilization and stabilization of spinal segments in patients (e.g., humans, dogs, cats, and other animals). Fixation devices may be used to help fuse bone segments (e.g., vertebrae) in the treatment of instabilities or deformities of, for example, the cervical, thoracic, lumbar, and/or sacral spine. Such instabilities or deformities may include, for example, degenerative disc disease (DDD); spondylolisthesis; trauma (i.e., fracture or dislocation); spinal stenosis; curvatures (i.e., scoliosis, kyphosis, and/or lordosis); tumor; pseudoarthrosis; and failed previous fusions.

FIGS. 1A, 1B, 1C, 1D, 1E depict a conventional spinal fixation system. FIG. 1A includes a fixation screw 101 located at the distal end of extension sleeve system, sometimes referred to as a "tulip". More specifically, screw 101 is included in the "saddle" 107, which couples to sleeves 102, 103. The sleeves are separated from each other by windows 105, 106. There is a circular recess 108 near the distal end of the system. FIG. 1B shows the same system as FIG. 1A but without screw 101 deployed in the saddle 107. FIG. 1C shows a side view of the same system. FIG. 1D shows a 90 degree rotation from the perspective of FIG. 1C. FIG. 1E shoes a close up of the proximal end of the system of FIG. 1B. Screw 101 may be deployed through orifice 109, down between sleeves 102, 103, and into saddle 107 and bone (e.g., pedicle, femur, humerus) that connects to saddle 107. Screw 101 may be inserted using an implant device, such as a screw driver, that is also inserted into orifice 109 or windows 105, 106. The two arms 102, 103 collectively couple to one another via ring portions 110, 111 at the proximal end of the tulip.

In greater detail, a physician slides screw 101 through the orifice 109 and into saddle 107. In some instances the screw may already be located in the saddle when the physician receives the system. After the screw is implanted into bone the physician will remove and/or break the ring portions 110, 111. By breaking the ring portions the proximal arms or sleeves 102, 103 are no longer directly connected to one another at the proximal end of the system. Instead, sleeves 102, 103 only indirectly couple to one another via saddle 107. So by breaking the ring portions 110, 111 (e.g., at one location 115 above window 105 and at another location 116 above the other slot or window 106), the proximal portions of arms 102, 103 may be moved independently of each other. Now the physician may "work" or bend back and forth the two arms 102, 103. Doing so helps fatigue the system at the distal ring 108 so that the arms break off from the saddle 107 at distal ring 108, thereby leaving only the saddle and screw in the patient. The two arms 102, 103 from the tulip may be removed.

BRIEF DESCRIPTION OF THE DRAWINGS

Features and advantages of embodiments of the present invention will become apparent from the appended claims, the following detailed description of one or more example embodiments, and the corresponding figures, in which:

FIG. 1A includes a fixation screw located at the distal end of an extension sleeve system. FIG. 1B shows the same system as FIG. 1A but without the screw. FIG. 1C shows a side view of the same system as FIG. 1A. FIG. 1D shows a 90 degree rotation from the perspective of FIG. 1C. FIG. 1E shoes a close up of the proximal end of the system of FIG. 1B.

FIG. 2A includes a fixation screw located at the distal end of an extension sleeve system. FIG. 2B shows the same system as FIG. 2A but without the screw. FIGS. 2C, 2D show different perspective views of proximal portions of the extended sleeve embodiment. FIGS. 2E, 2F show side views of proximal portions of the extended sleeve embodiment. FIGS. 2G, 2H show front and rear views of proximal portions of the extended sleeve embodiment. FIGS. 2I, 2J show dimensions of proximal portions of an embodiment of the extended sleeve system.

FIG. 4A includes a fixation screw located at the distal end of an extension sleeve system. FIG. 4B shows the same system as FIG. 4A but without the screw. FIG. 4C shows a different perspective of FIG. 4B. FIGS. 4D, 4E show different perspective views of proximal portions of the extended sleeve embodiment.

FIG. 5A depicts three tulip structures with protective proximal rings already removed. FIG. 5B shows the physician accessing the channels between sleeves for all three of the tulip structures.

FIG. 5C shows the physician implanting a linkage rod that will link three different pedicle screws.

FIG. 7A depicts two tulip structures with protective proximal rings still present. FIG. 7B shows the physician accessing the channels between sleeves for both of the tulip structures. FIG. 7C shows the physician implanting a linkage rod that will link two different pedicle screws.

DETAILED DESCRIPTION

In the following description, numerous specific details are set forth but embodiments of the invention may be practiced without these specific details. Well-known structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical contact. Also, while similar or same numbers may be used to designate same or similar parts in different figures, doing so does not mean all figures including similar or same numbers constitute a single or same embodiment.

Figure 1A:
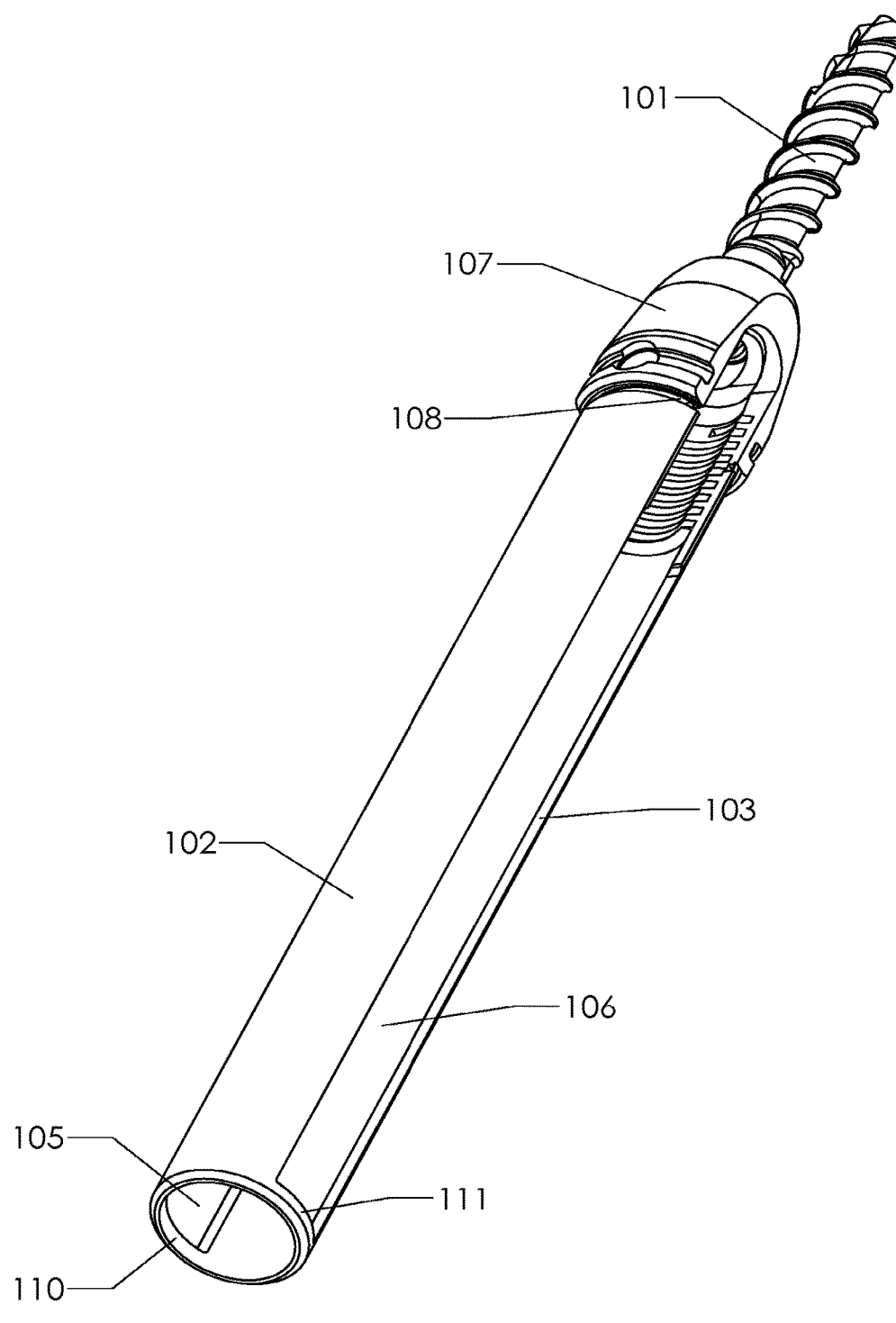
FIGS. 1A, 1B, 1C, 1D, 1E depict a conventional spinal fixation system.
Figure 1B:
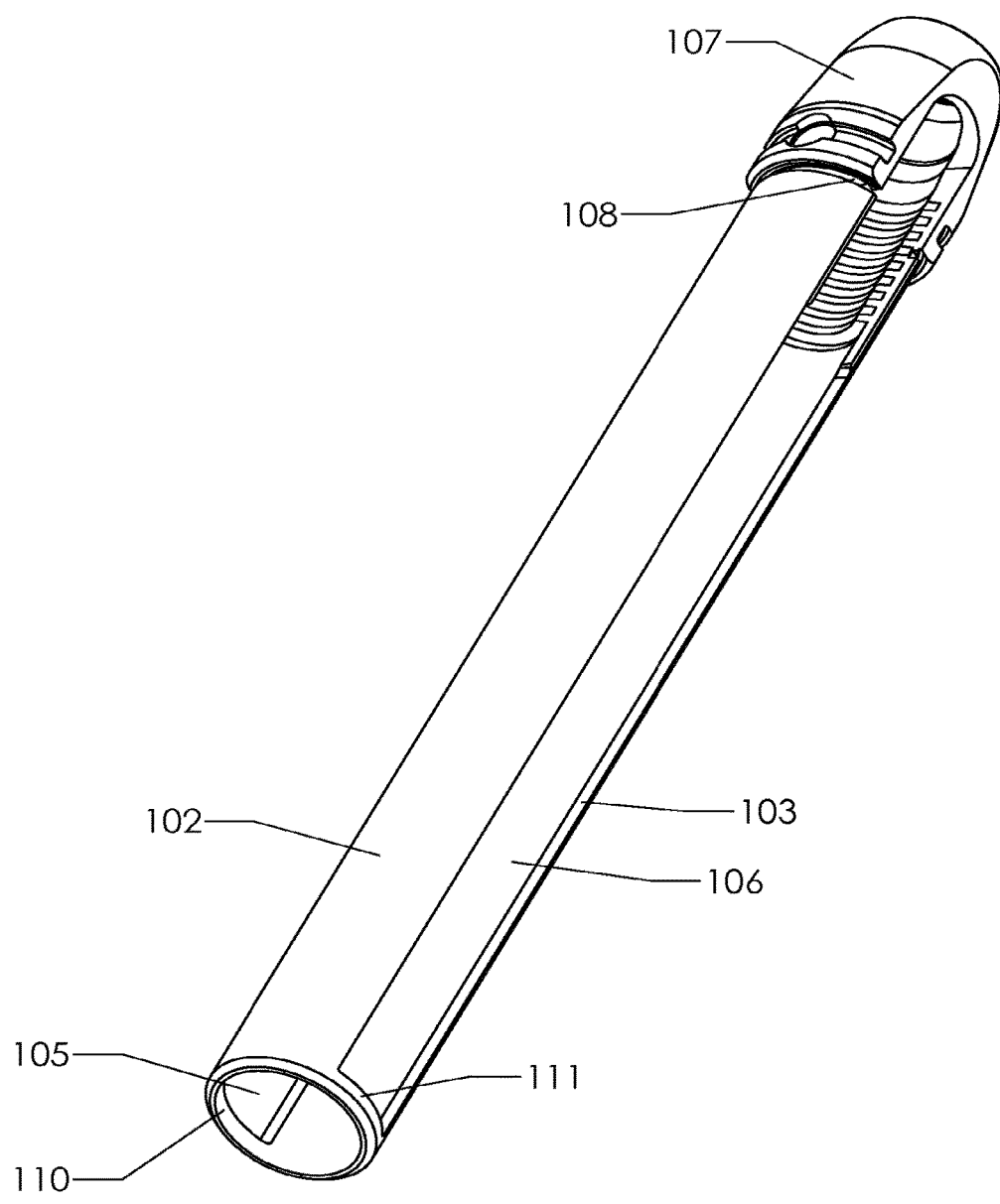
Figure 1C:
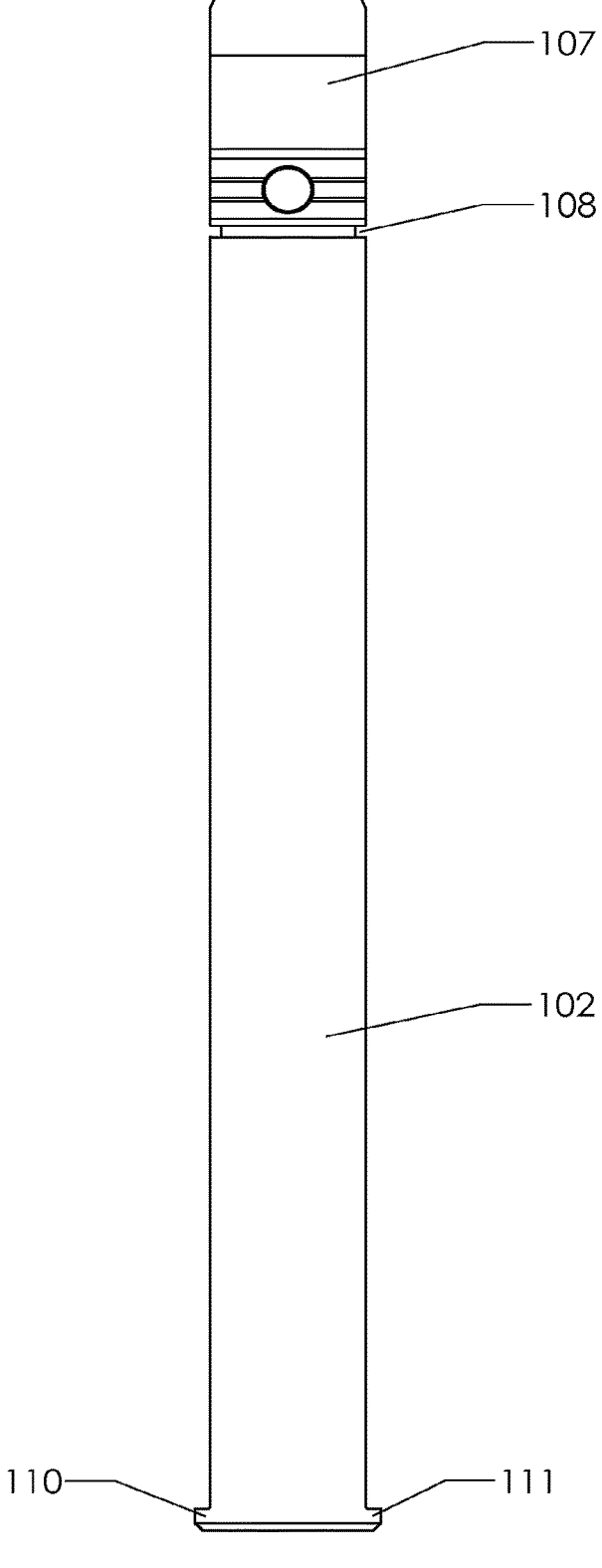
Figure 1D:
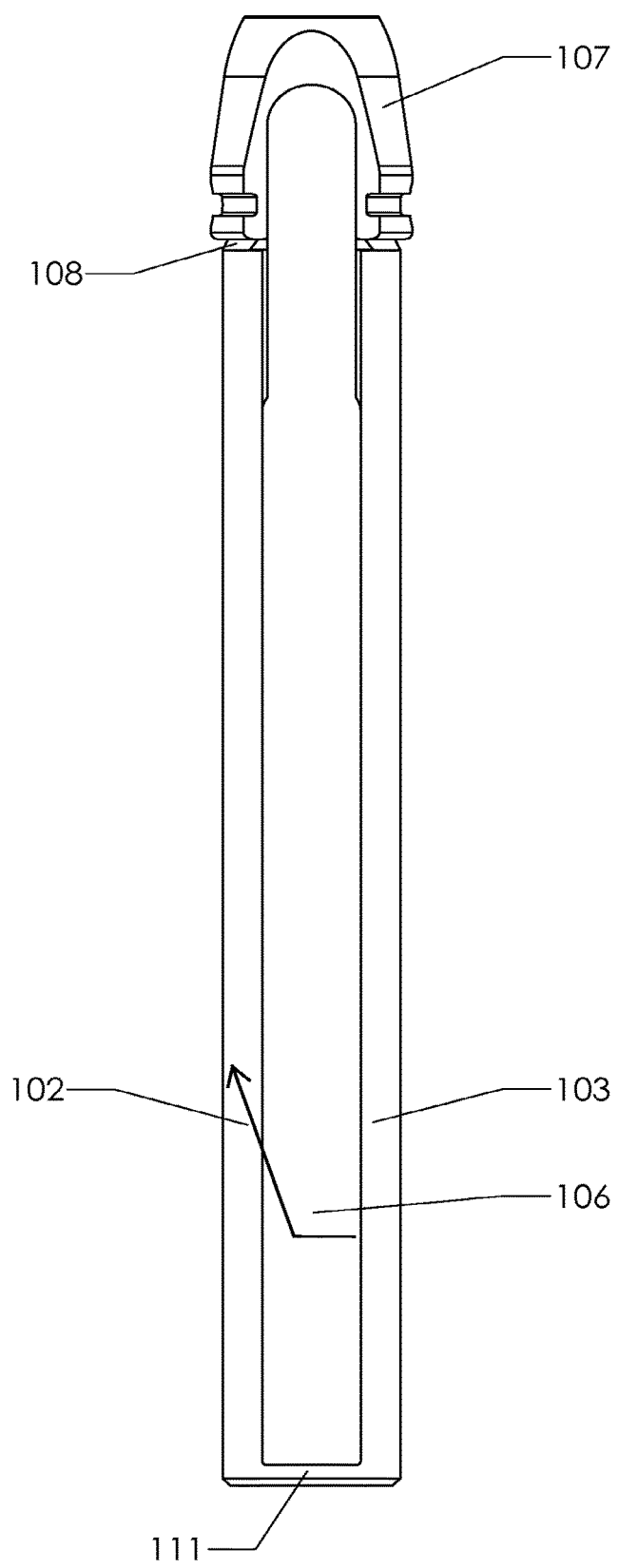
Figure 1E:
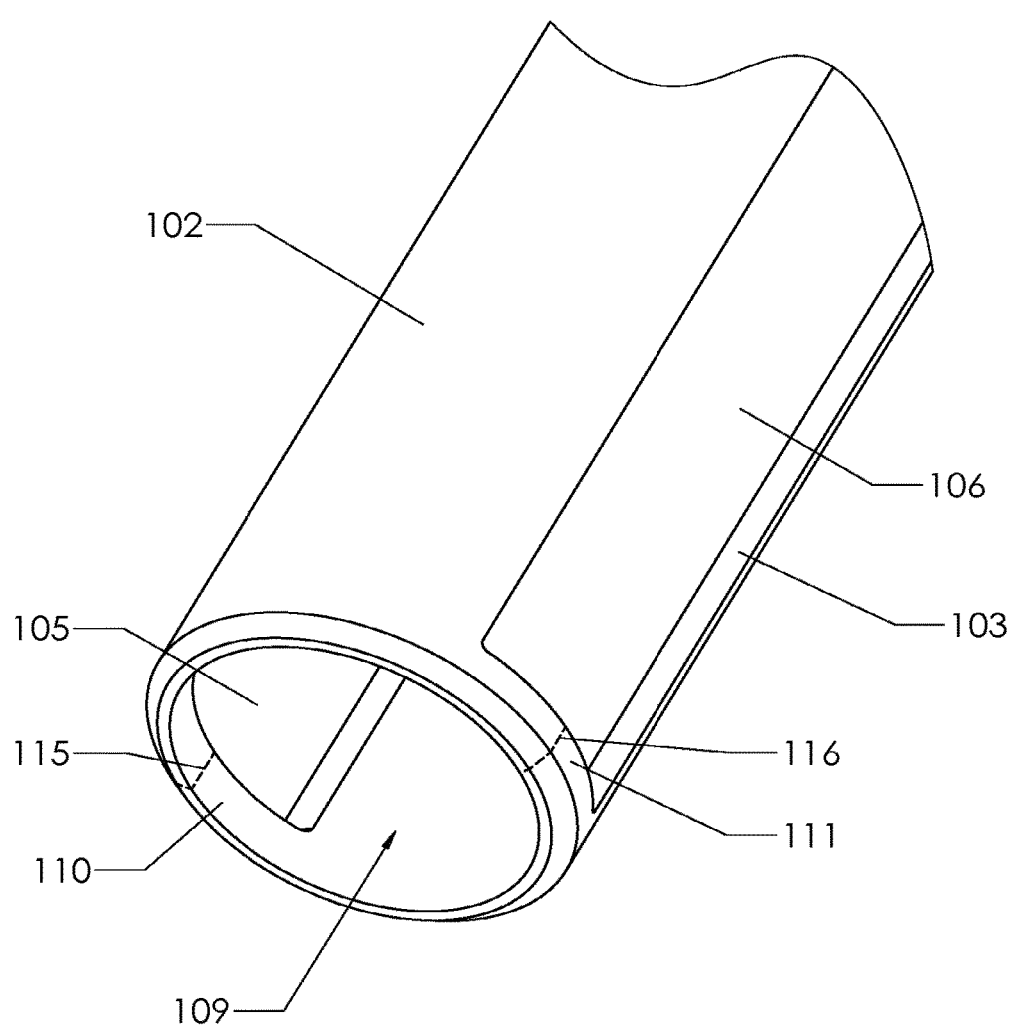

As described above with regard to FIGS. 1A, 1B, 1C, 1D, 1E, modular extended tulips are used for minimally invasive spine surgery. The various types of tulips range from flexible snap on tulips to fixed one-piece tulips. A problem with the modular based tulip extensions is that they have a tendency to release from the tulip or saddle unexpectedly. A problem with existing fixed one-piece tulips is that they are either too flexible and/or they are difficult to separate at their tops prior to breaking the tulips off from pedicle screws at the end of the surgery. The existing fixed one-piece tulips require additional steps to separate. Generally, they require the surgeon to cut the joining piece on the tulips, such as portions 110, 111 of FIG. 1E. This necessitates an additional surgical step and also opens the potential for leaving a remnant of the tulip in the patient or leaving a sharp remnant that can cut the surgeon or patient. For example, a physician that cuts each of 110 and 111 in half (for example, at areas 115, 116) will then have sharp edges at these cut points. Specifically, there will be two sharp points at the cut line 116 in member 111 and there will be two sharp points at the cut line 115 in member 110. Furthermore, the sharp points will be exposed and unprotected as the arms 102, 103 are moved away from each other. The sharp points pose a hazard to the physician, the operating personnel (e.g., scrub nurses), and the patient.

In contrast to conventional systems, an embodiment of the invention includes a minimally invasive pedicle screw system consisting of an extended 5.75" fixed one-piece titanium tulip (e.g., FIG. 2A) with a special milling pattern (e.g., portions 220, 221, 222 addressed below) combined with a cannulated screw. Other embodiments are not limited to 5.75" dimensions and may be shorter, longer, wider, and/or skinnier. This allows a screw to be inserted into the surgical site over a k-wire through a very small surgical incision. The extended tulip arms aid in both the retraction of soft tissue as well as helping the surgeon to visualize the orientation of the screws in the body space.

Figure 2A:
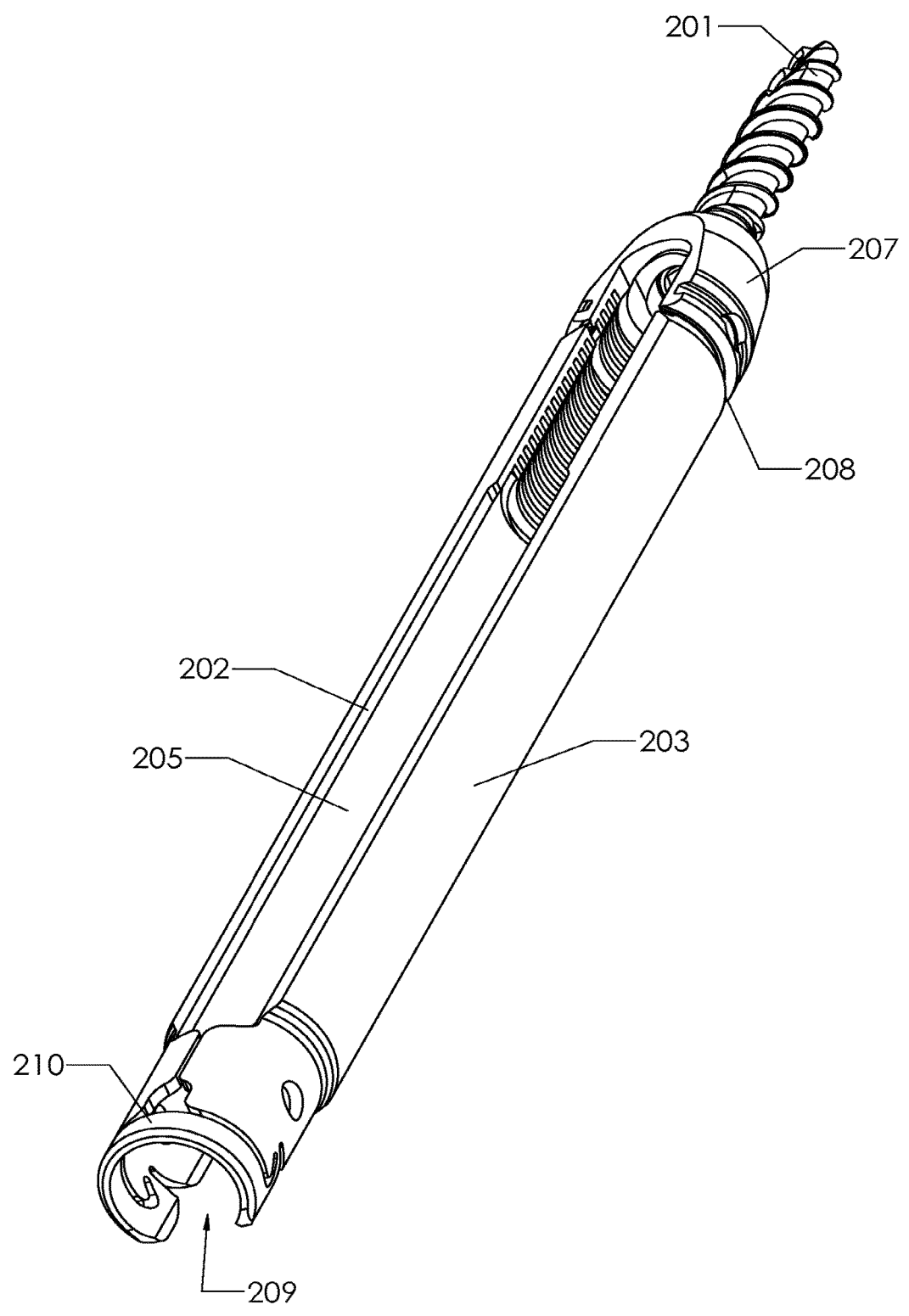
FIGS. 2A, 2B, 2C, 2D, 2E, 2F, 2G, 2H, 2I, 2J depict an embodiment of the invention.

An embodiment of the extended sleeve system consists of a very rigid one piece tulip (e.g., FIG. 2A). It is completely joined at the top by a circular ring of titanium (210) that is generated (e.g., milled) from the actual tulip arms themselves. The circular ring has a unique undercut 250 that allows the surgeon to remove the ring when he wishes by simply lifting up on the ring 210. The ring's unique undercut geometry 250 allows the ring to release easily when the surgeon desires. The undercut also prevents leaving any sharp remnants that can cut the surgeons hands or cause any trauma to the patient. For example, any sharp edge left at fracture point 216 is protected or shielded by projections 221, 222. This helps protect the physician, operating personnel, and the patient from sharp edge at fracture point 216.

Figure 2B:
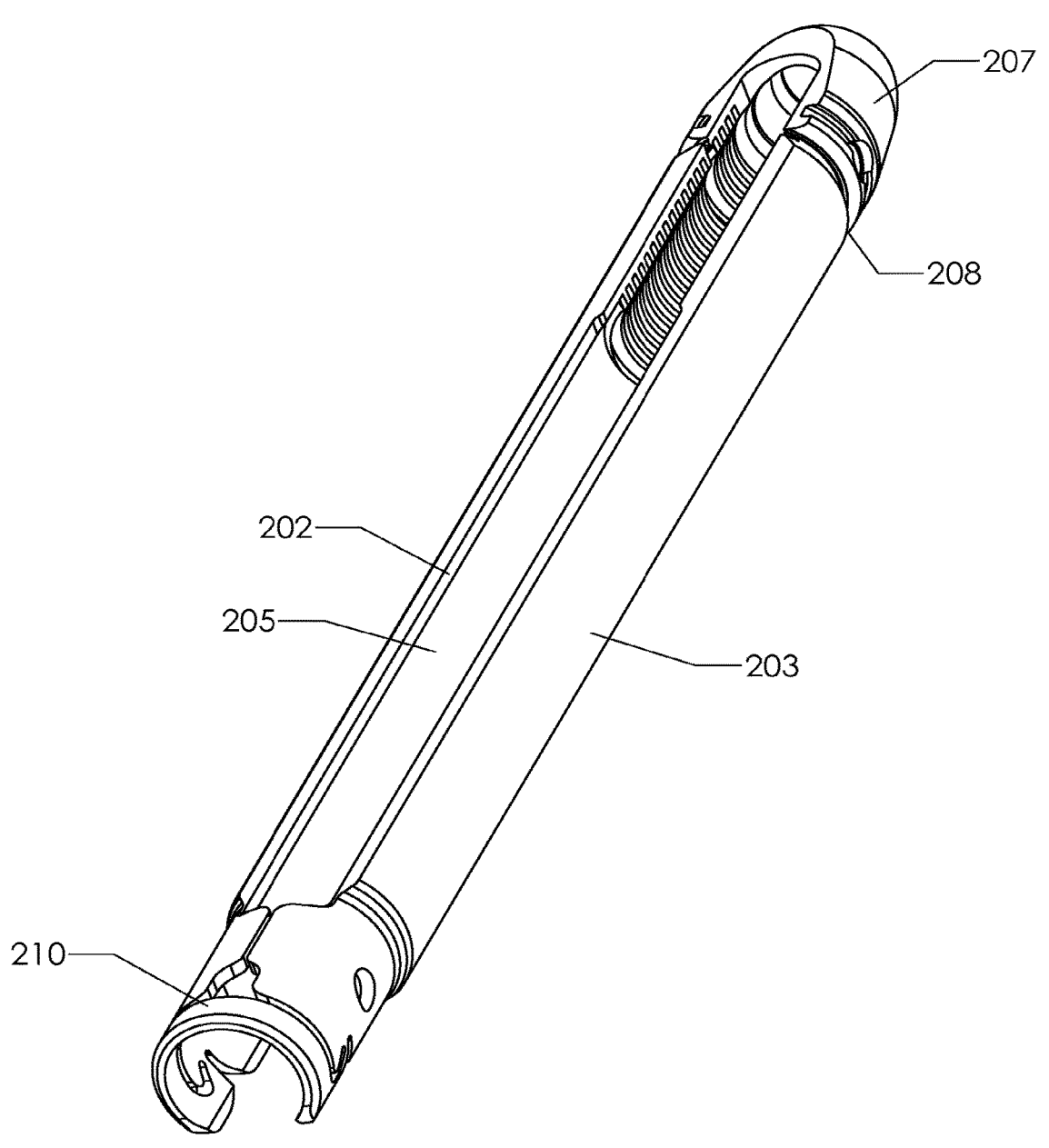

A more detailed discussion of an embodiment of the invention, as shown in FIGS. 2A-2J, now follows. FIG. 2A includes screw 201 located at the distal end (e.g., saddle 207) of a tulip. FIG. 2B shows the tulip without a screw. A circular recess 208 is near the distal end of the system, directly adjacent saddle 207, which provides a weakened and thinned portion that may be fatigued in order to separate arms 202, 203 from the system. Windows or slots 205, 206 receive the screw and a driver, such as a screw driver, for implanting the screw into tissue (e.g., bone). The slots separate arms 202, 203 from each other. The arms collectively couple the proximal end of the tulip to the distal end of the tulip. Ring 210 is at the proximal end of the system.

In practice, the physician slides screw 2-1 through the orifice 209, into the distal end of the tulip, and then into saddle 207. (In other embodiments the screw may already be located in the distal end of the system when the physician receives the system.) After the screw is implanted into bone the physician will remove the ring 210 at the proximal end of the system and then fatigue the system at the distal ring 208 so that the arms 202, 203 break off.

Figure 2C:
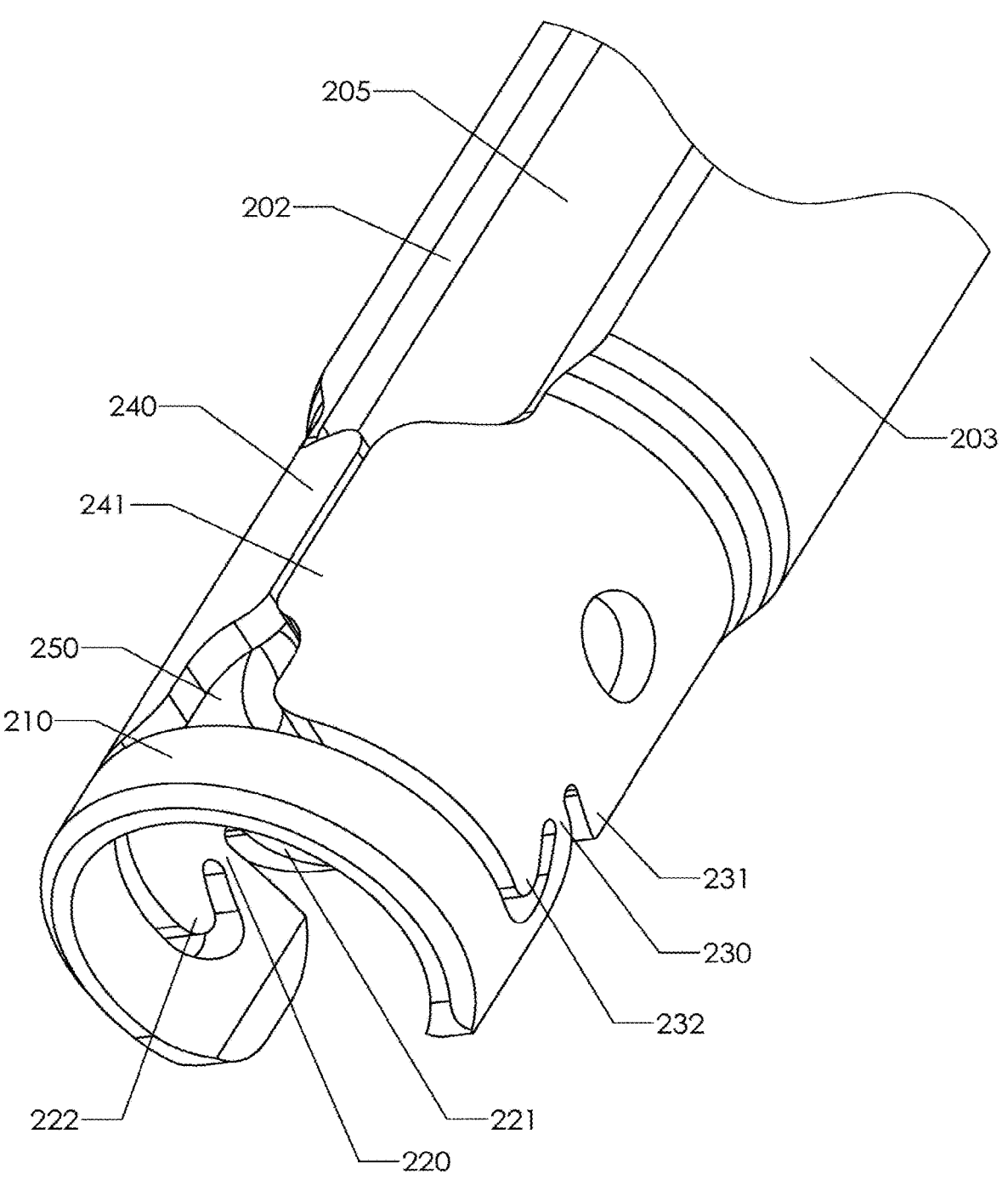
Figure 2D:
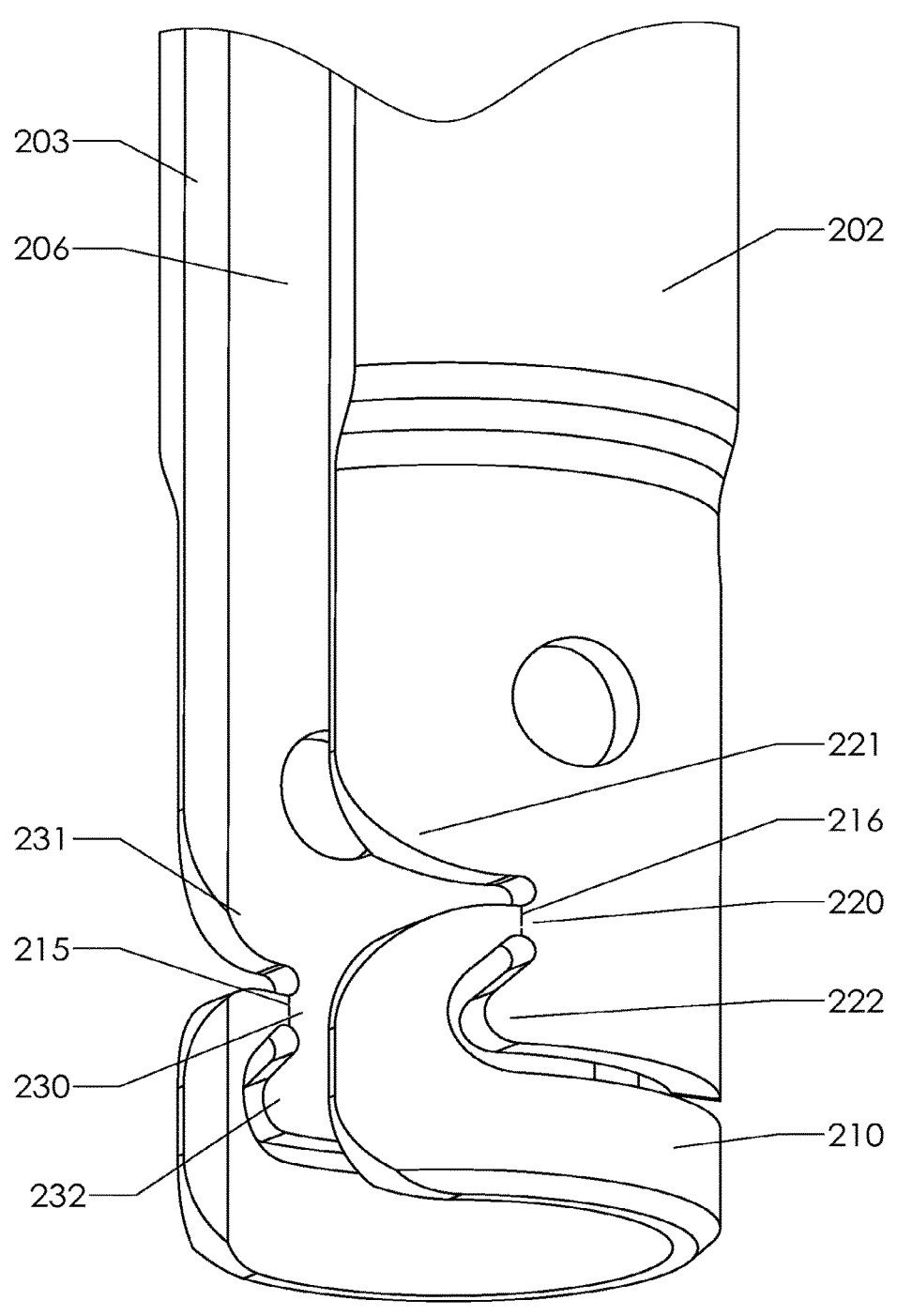
Figure 2E:
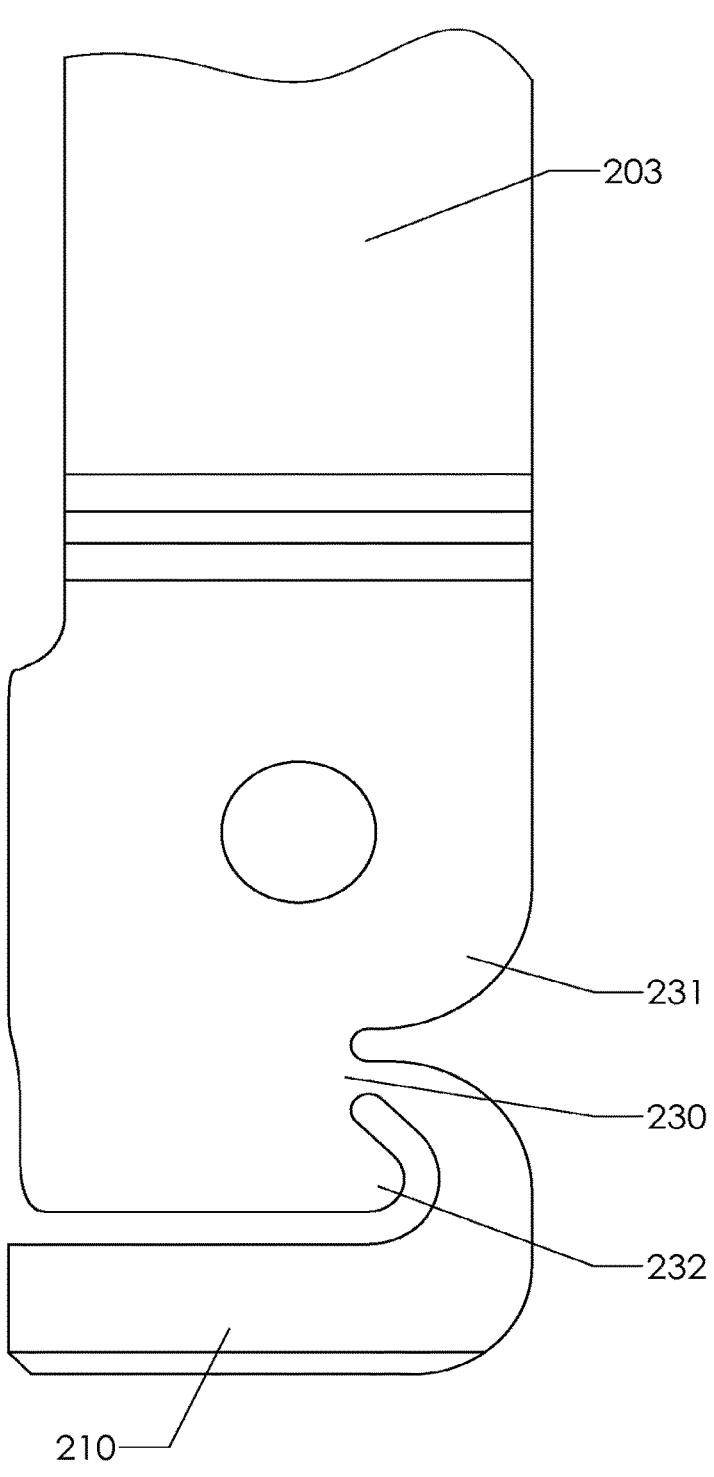
Figure 2F:
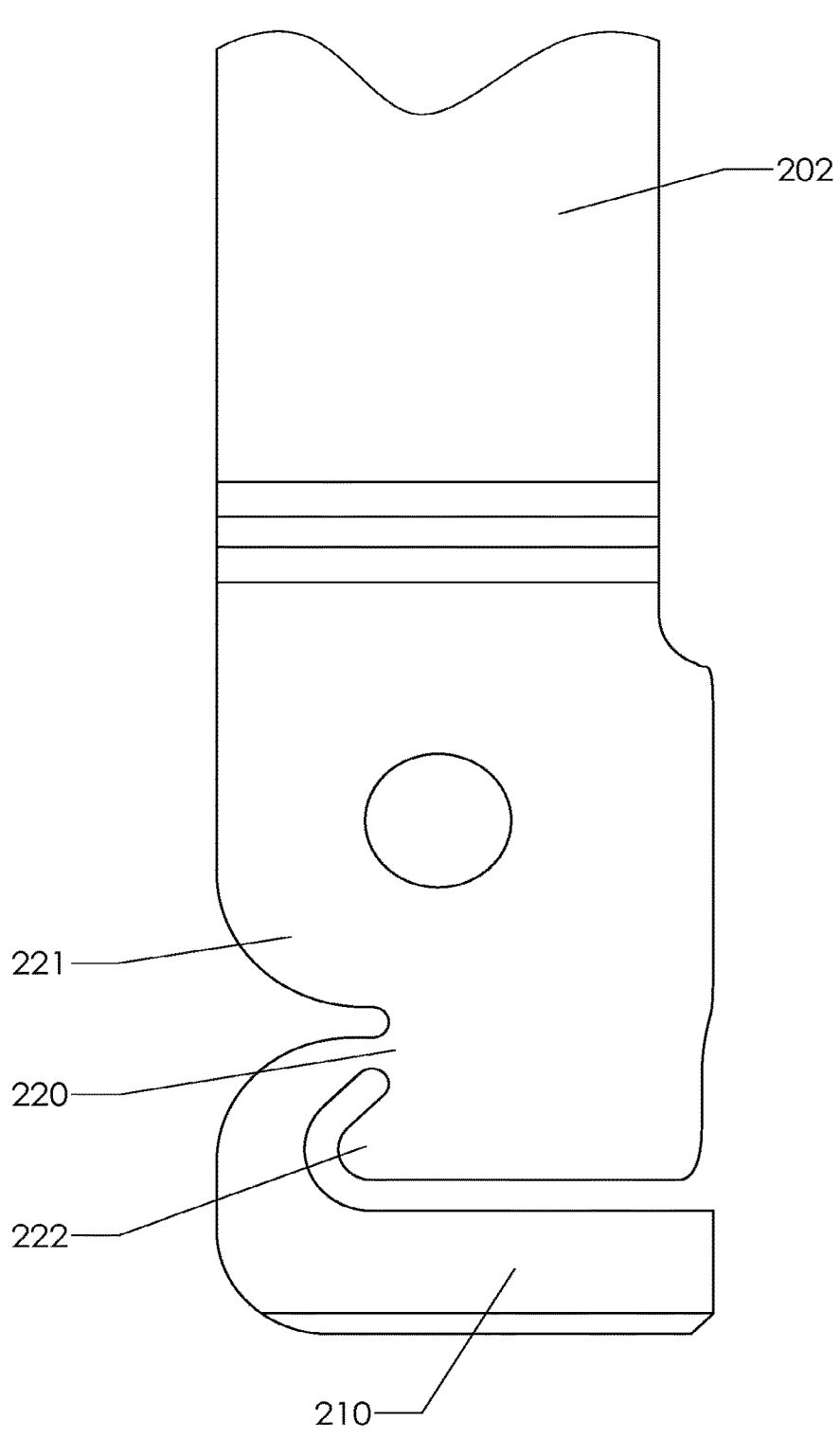
Figure 2G:
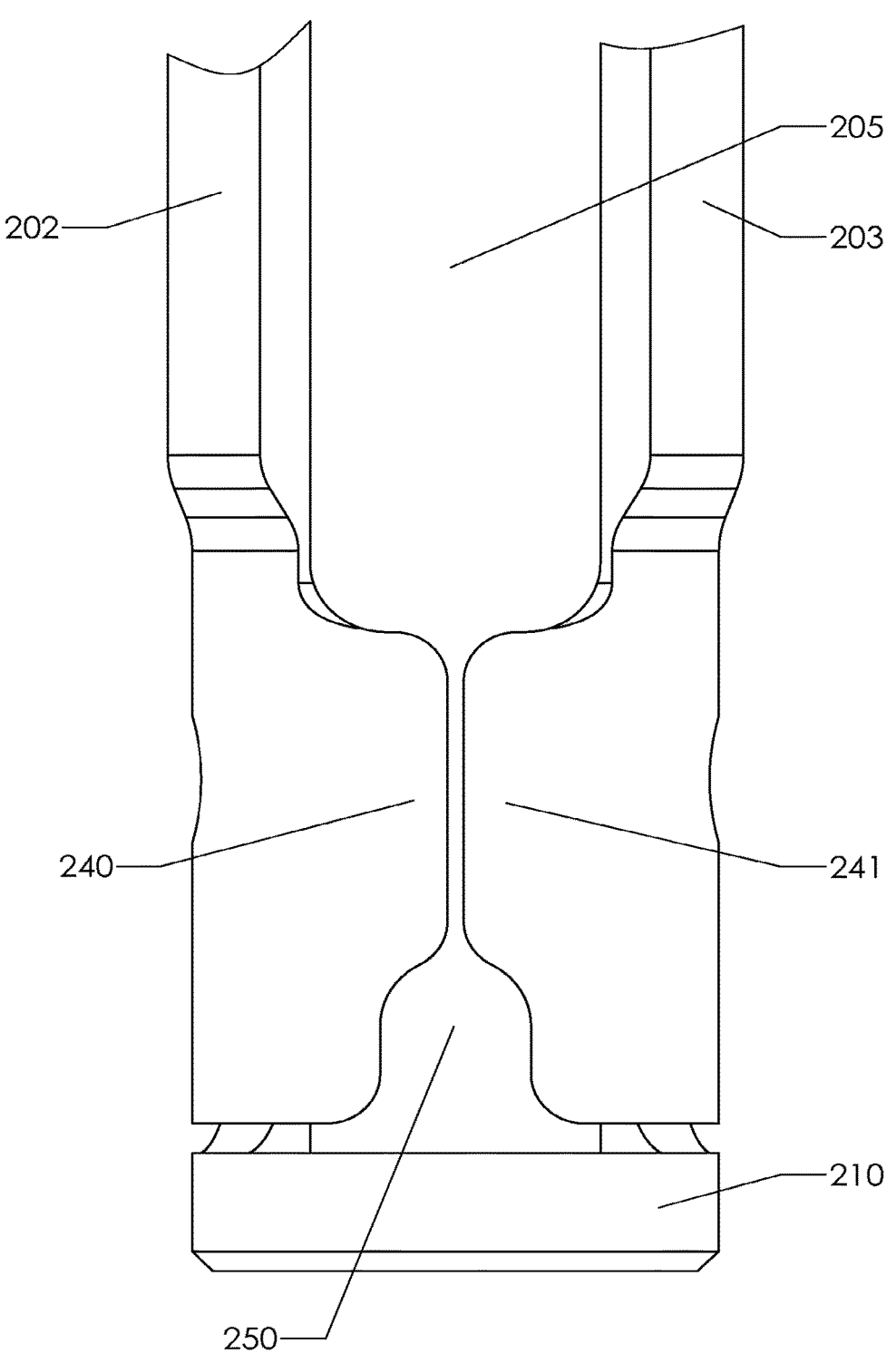
Figure 2H:
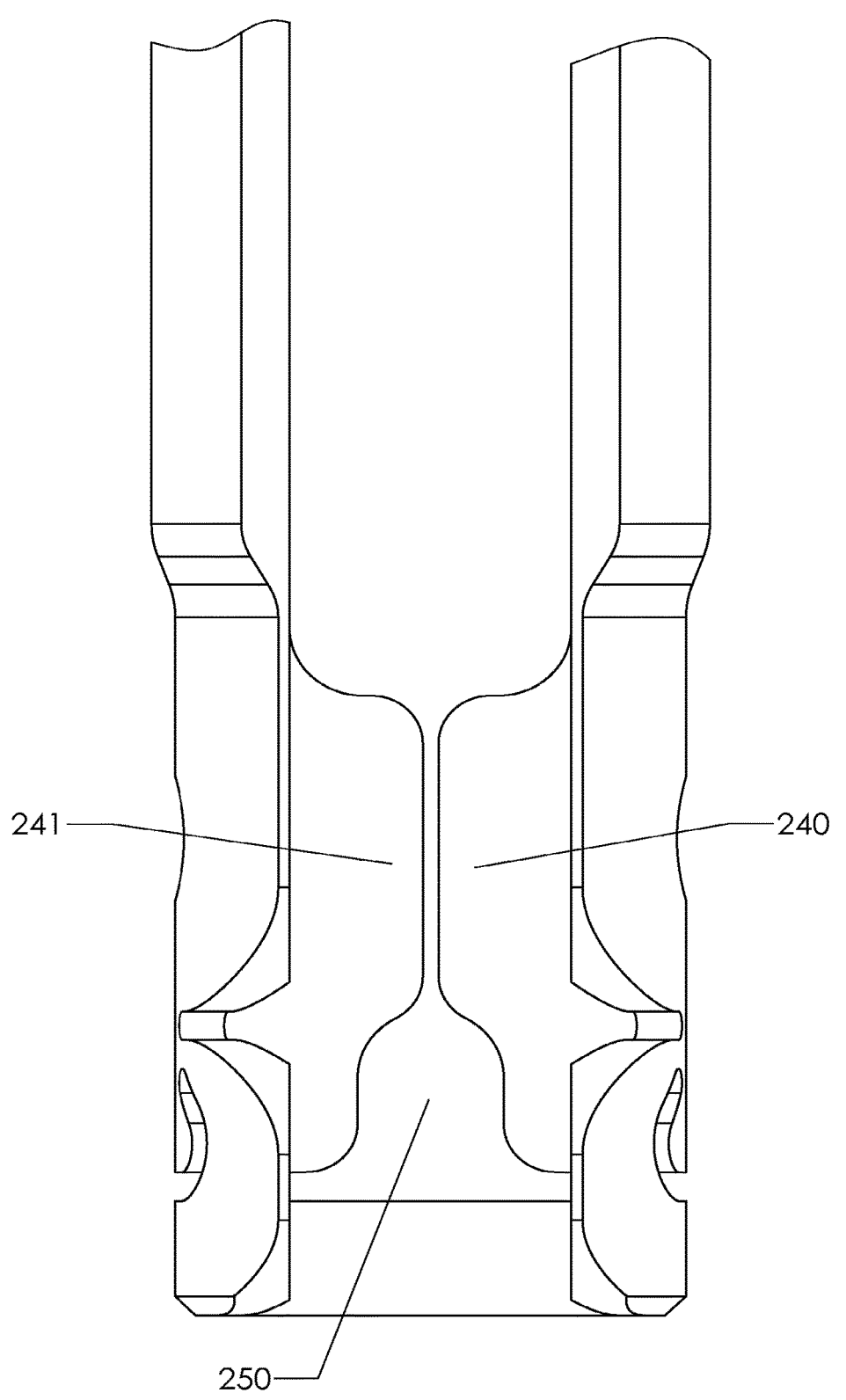

As shown in FIG. 2C, an embodiment includes a novel proximal end that is easy for a physician to couple an instrument to and to then move the tulip about. The proximal end breaks off relatively easily due to the low area of contact between the proximal ring 210 and the arms 202, 203. Specifically, in an embodiment the proximal end includes ring 210 that joins arms 202, 203 at thin locations 220, 230. Void 250 provides a space for a physician to grip member 210 with forceps and the like. The member 210 is then rotated away from sleeves 202, 203 directing torque to locations 215, 216 (see FIGS. 2D, 2E). These thinned areas fail, providing a sharp edge at locations 215, 216 (see FIG. 2I). However, location 215 is protected by protuberances or projections 231, 232 and location 216 is protected by protuberances or projections 221, 222.

In an embodiment tabs 240, 241 (FIG. 2C) are located on proximal portions of sleeves 202, 203 to provide stability to the system (e.g., when members 202, 203 are compressed towards one another) before and after removal of member 210. Other embodiments do not include these tabs or projections.

Figure 2I:
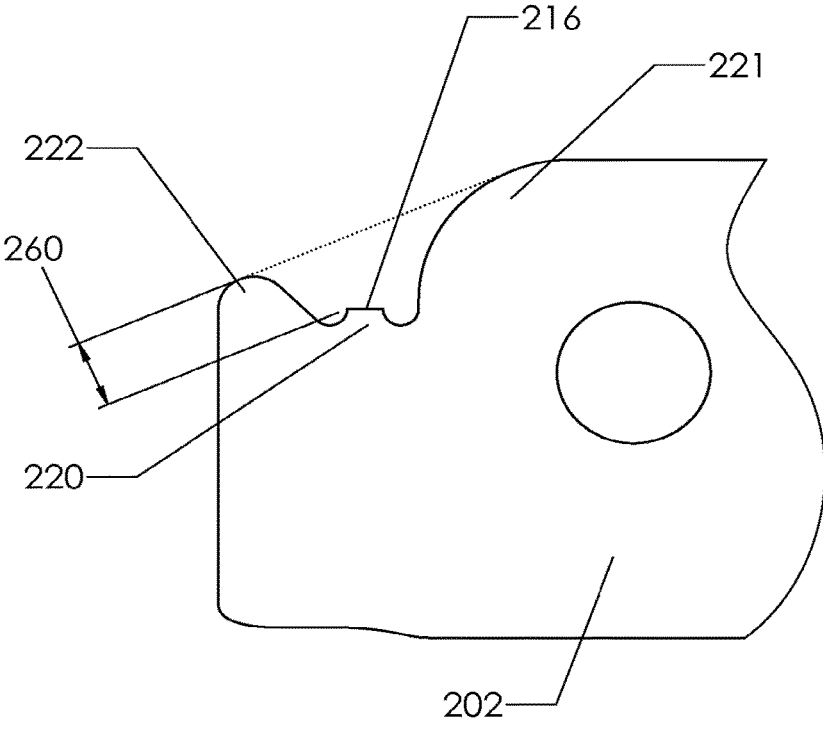

FIG. 2I illustrates an embodiment after ring 210 has been removed. Sharp edge 216 is protected by rounded and smooth extensions 221, 222. Dimension 260 indicates an embodiment that provides 1.6 mm (0.06 inches) of clearance between sharp edge 216 and a space extended beyond the protection of extensions 221, 222 (however in other embodiments 260 is 0.5, 1, 1.5, 2, 2.5, 3 or more mm.

Figure 2J:
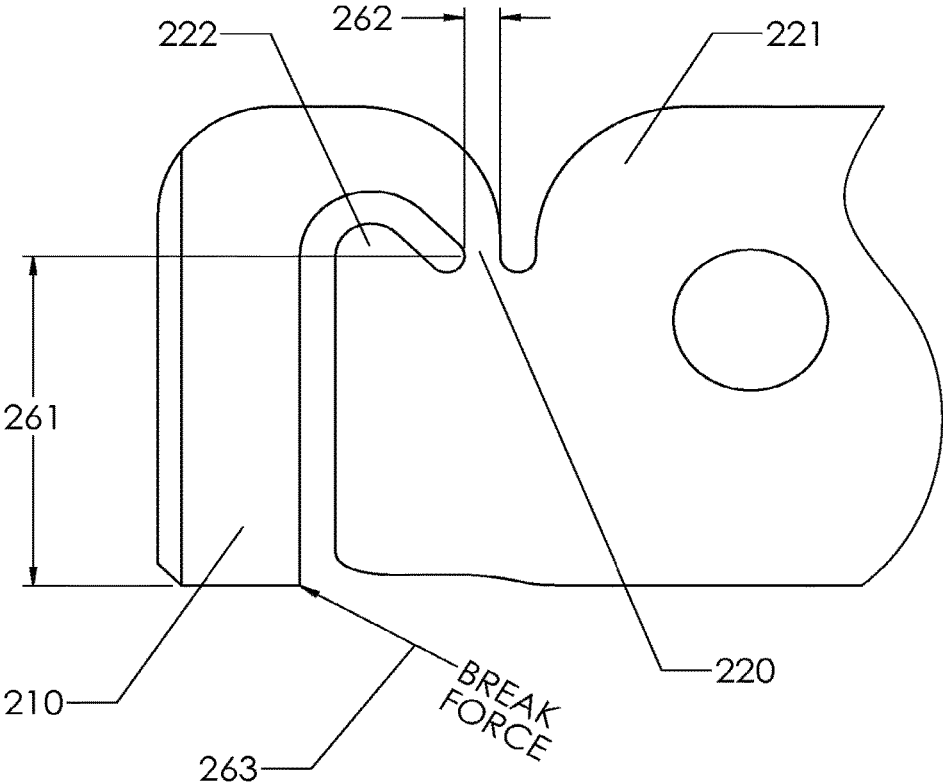

FIG. 2J illustrates an embodiment before ring 210 has been removed. Area 220 is thinned in comparison to other portions of the system, thereby promoting failure at that location. In embodiment area 220 is 0.8 mm in diameter (see dimension 262). In other embodiments dimension 262 is 0.4, 0.5, 0.6, 0.7, 0.9, 1.0, 1.1 or more mm. A portion of ring 210 serves as a moment arm to generate torque at location 220. The moment arm, extending from pivot point or fulcrum 220 to the outer portion of the arm, is 7.7 mm (see dimension 261). In other embodiments dimension 261 is 5, 6, 7, 8, 9, 10, 11 or more mm. These dimensions, in relation to one another, are critical (in one embodiment) to generate enough torque (dependent on moment arm length) to provide failure (dependent on thinned portion 220) without undue effort from the physician while also providing stability without unwanted failure at location 220 while the physician works with the system. In an embodiment a torque of 8-10 pounds force is generated to force failure of area 220. In an embodiment the moment to break the tab would be the force multiplied by the distance over which it is applied or 2.4-3.0 inch-pounds.

Figure 3A:
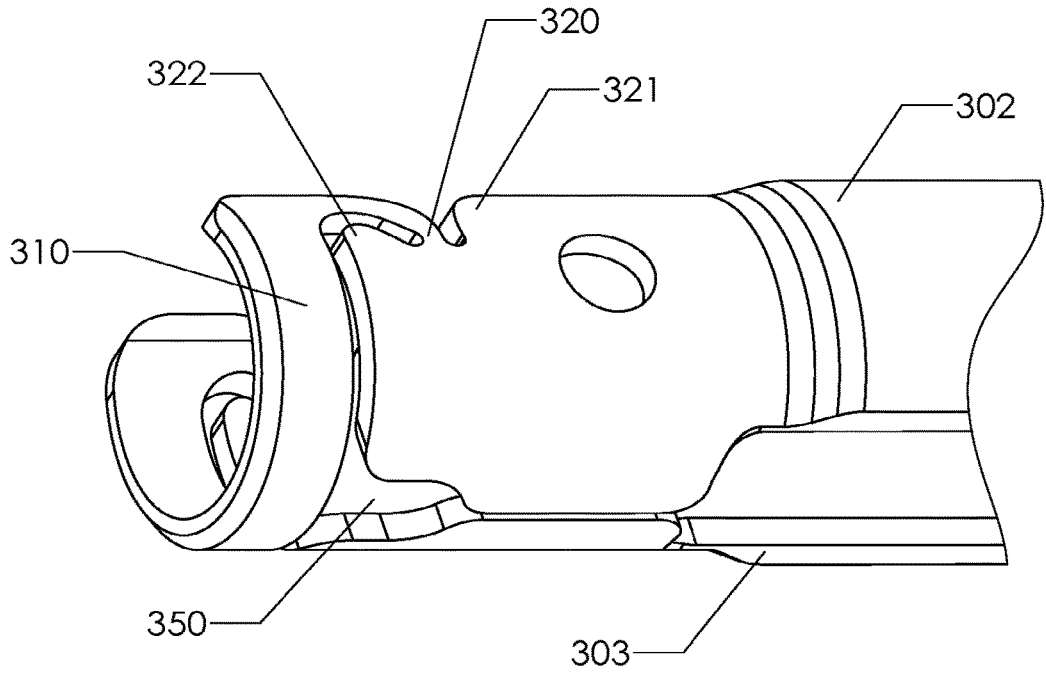
FIG. 3A shows a proximal end of a sleeve system before a linking ring is removed and the proximal ends of sleeves are disconnected from one another.
Figure 3B:
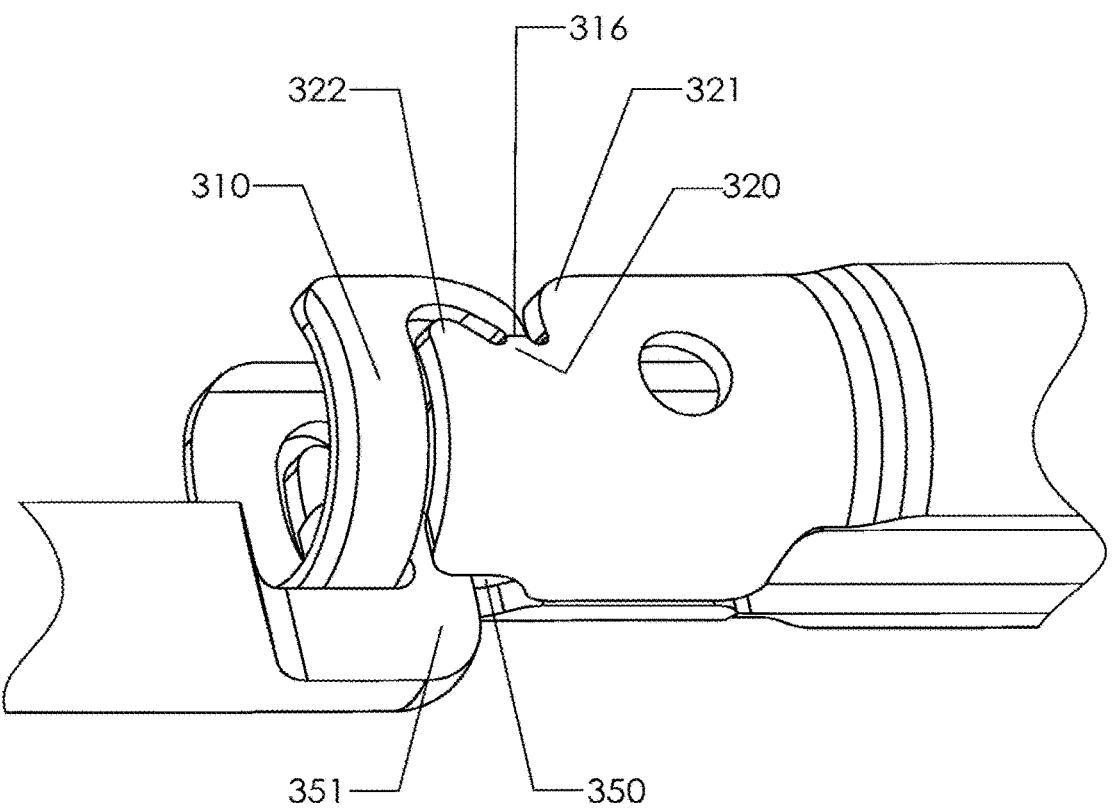
FIG. 3B shows a hook member seizing the proximal linking ring.
Figure 3C:
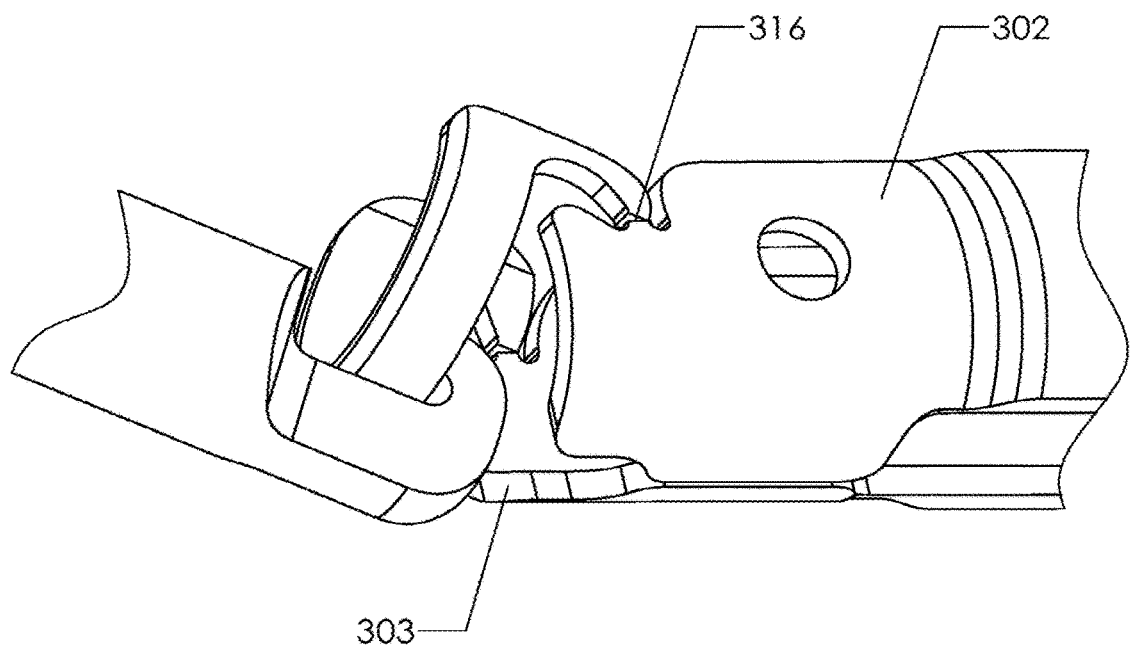
FIG. 3C shows the hook member pulling on the linking ring thereby causing a fracture at thin portions of the sleeves.
Figure 3D:
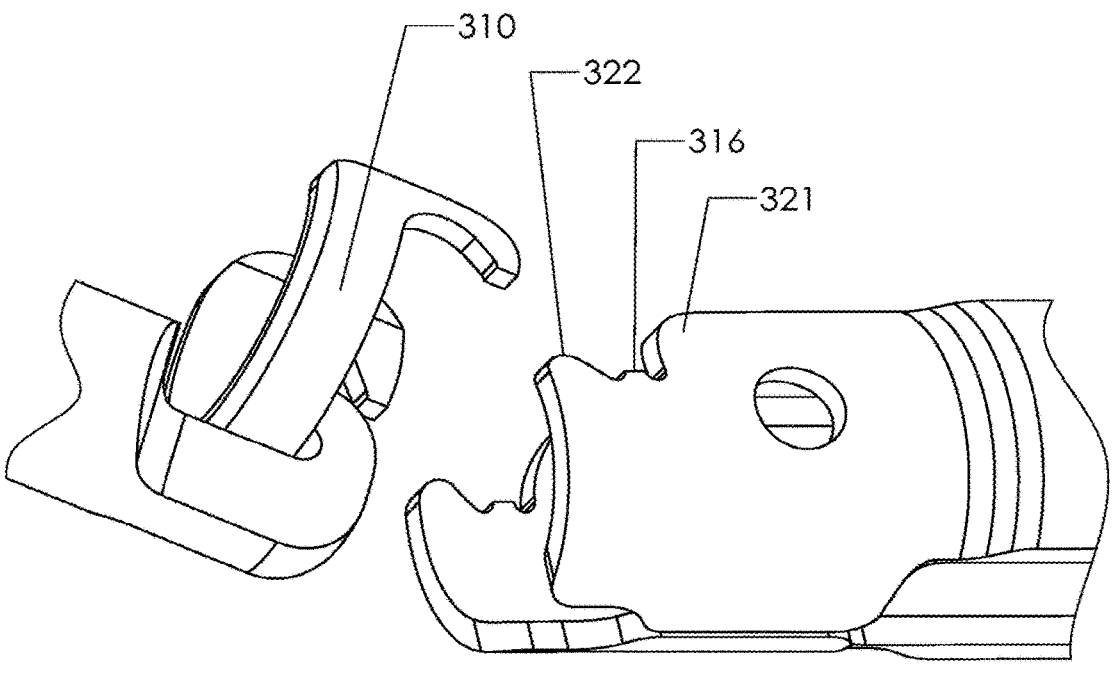
FIG. 3D shows the system after the linking ring has been removed thereby leaving a sharp edge protected by protrusions on either side of the sharp edge.

FIG. 3A shows a proximal end of a sleeve system before a linking ring is removed and the proximal ends of sleeves are disconnected from one another. Specifically, ring 310 couples portion 320 of sleeve 302 to a similarly thinned portion (not shown) on sleeve 303. Thin portion 320 is adjacent protrusions 321, 322. FIG. 3B shows a hook member seizing the linking ring by placing hook member 351 into void 350. In other embodiments forceps, grasps, pliers, and the like may be used to grasp or secure member 310. FIG. 3C shows the hook member pulling on the linking ring 310, thereby causing a fracture at thin portions of the sleeves (e.g., at location 316 of arm 302 and corresponding thinned location on arm 303). FIG. 3D shows the system after the linking ring 310 has been removed thereby leaving a sharp edge 316 protected by protrusions 321, 322 on either side of the sharp edge 316.

Figure 4A:
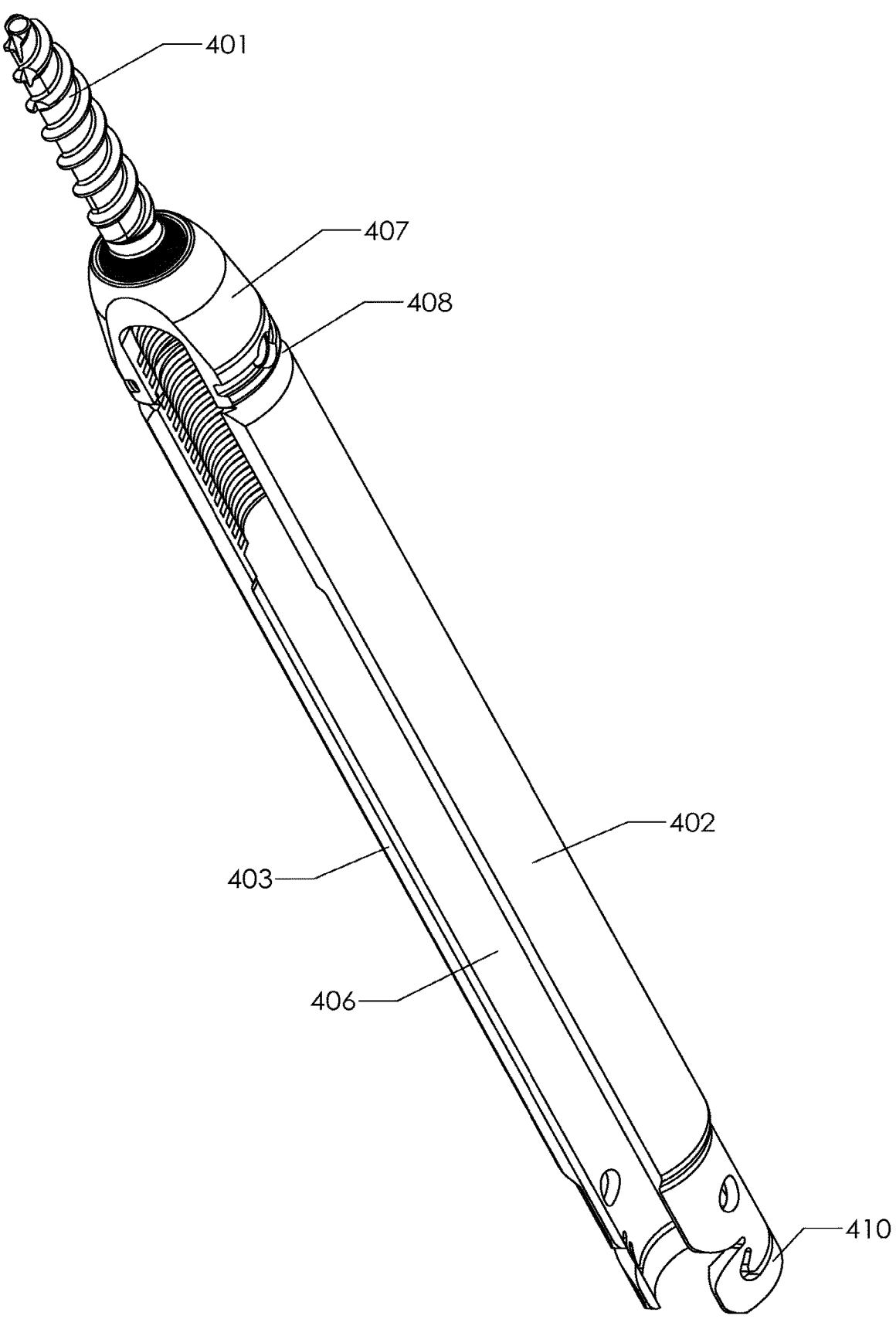
FIGS. 4A, 4B, 4C, 4D, 4E depict an embodiment of the invention.
Figure 4B:
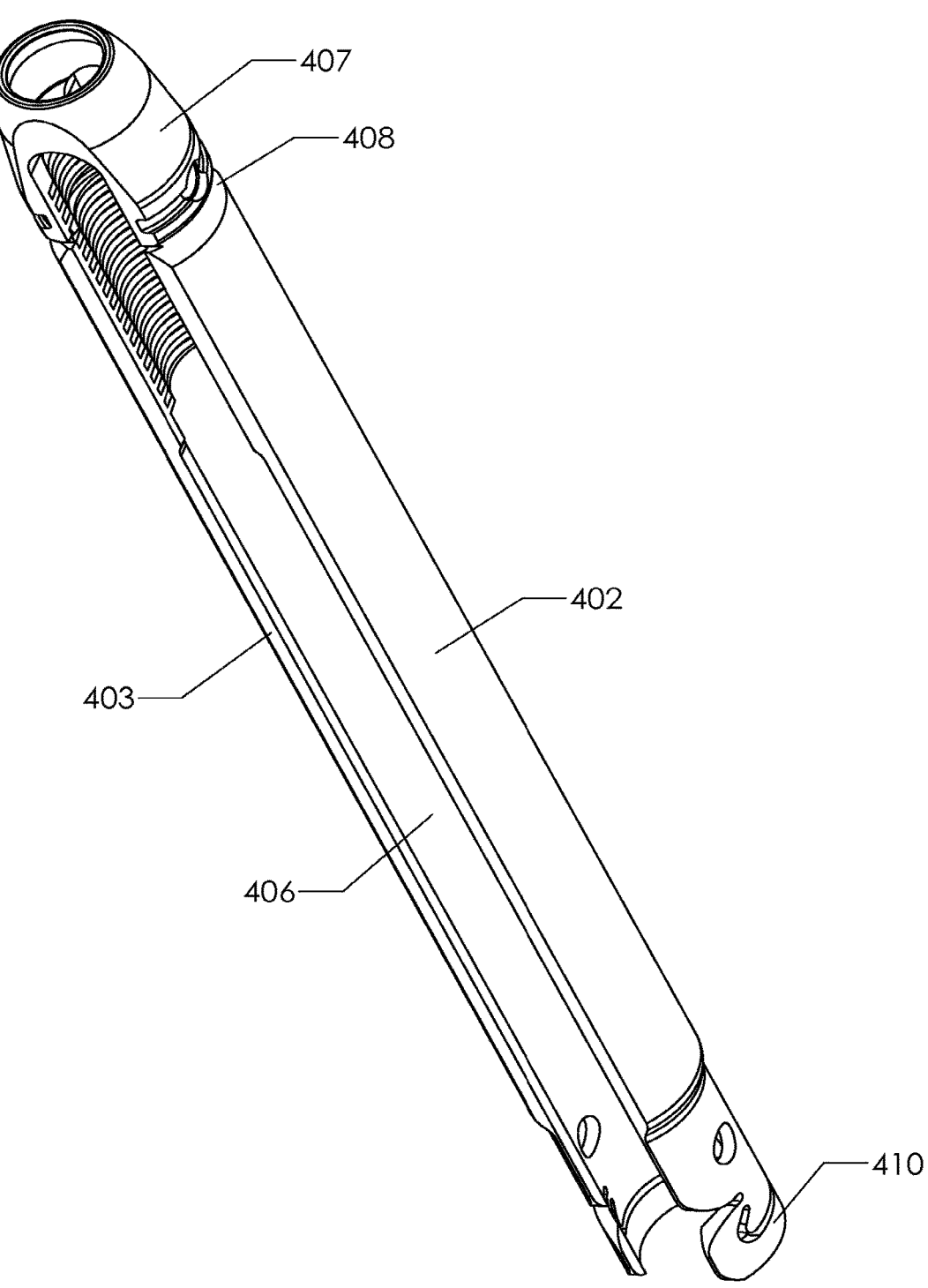
Figure 4C:
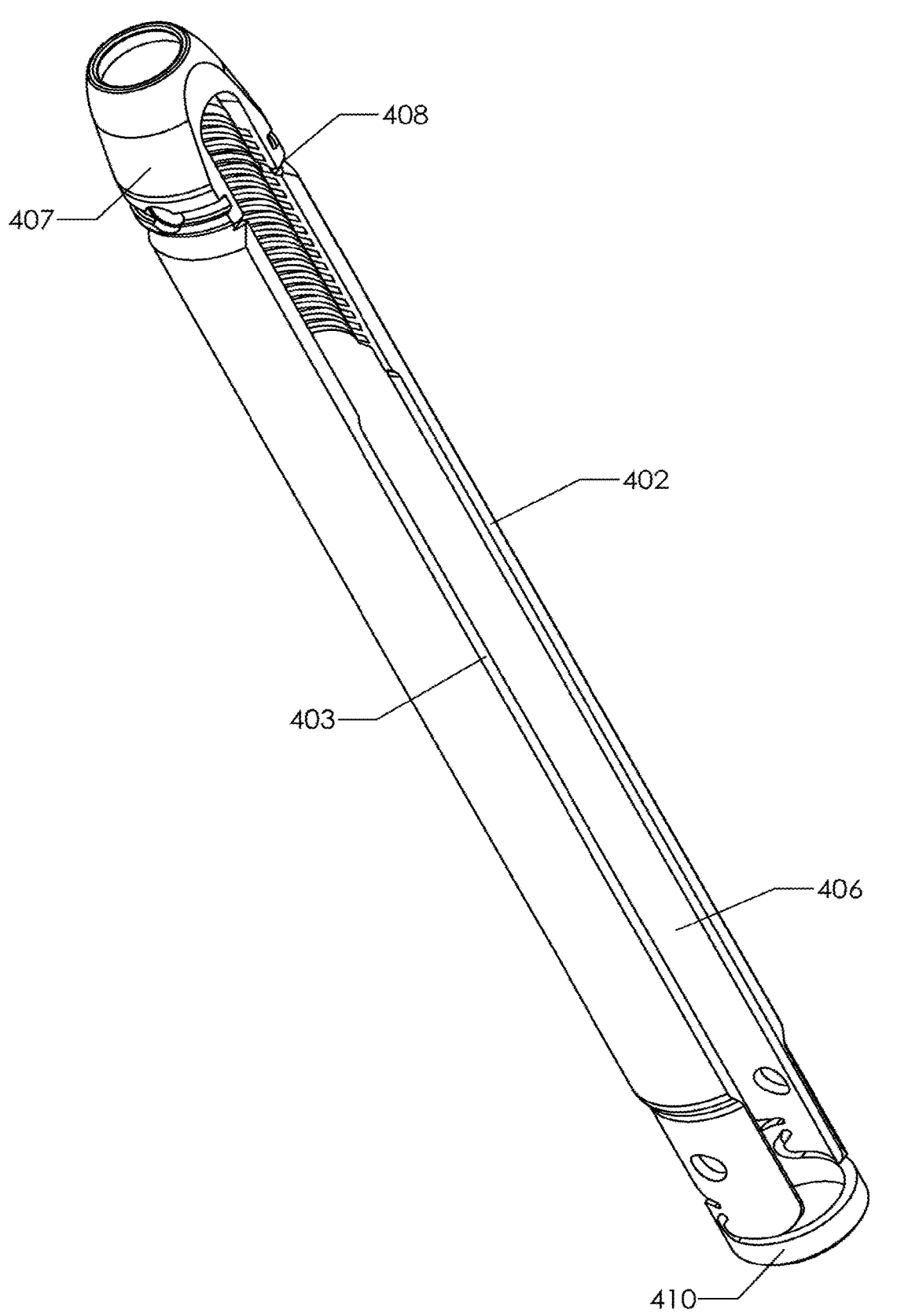
Figure 4D:
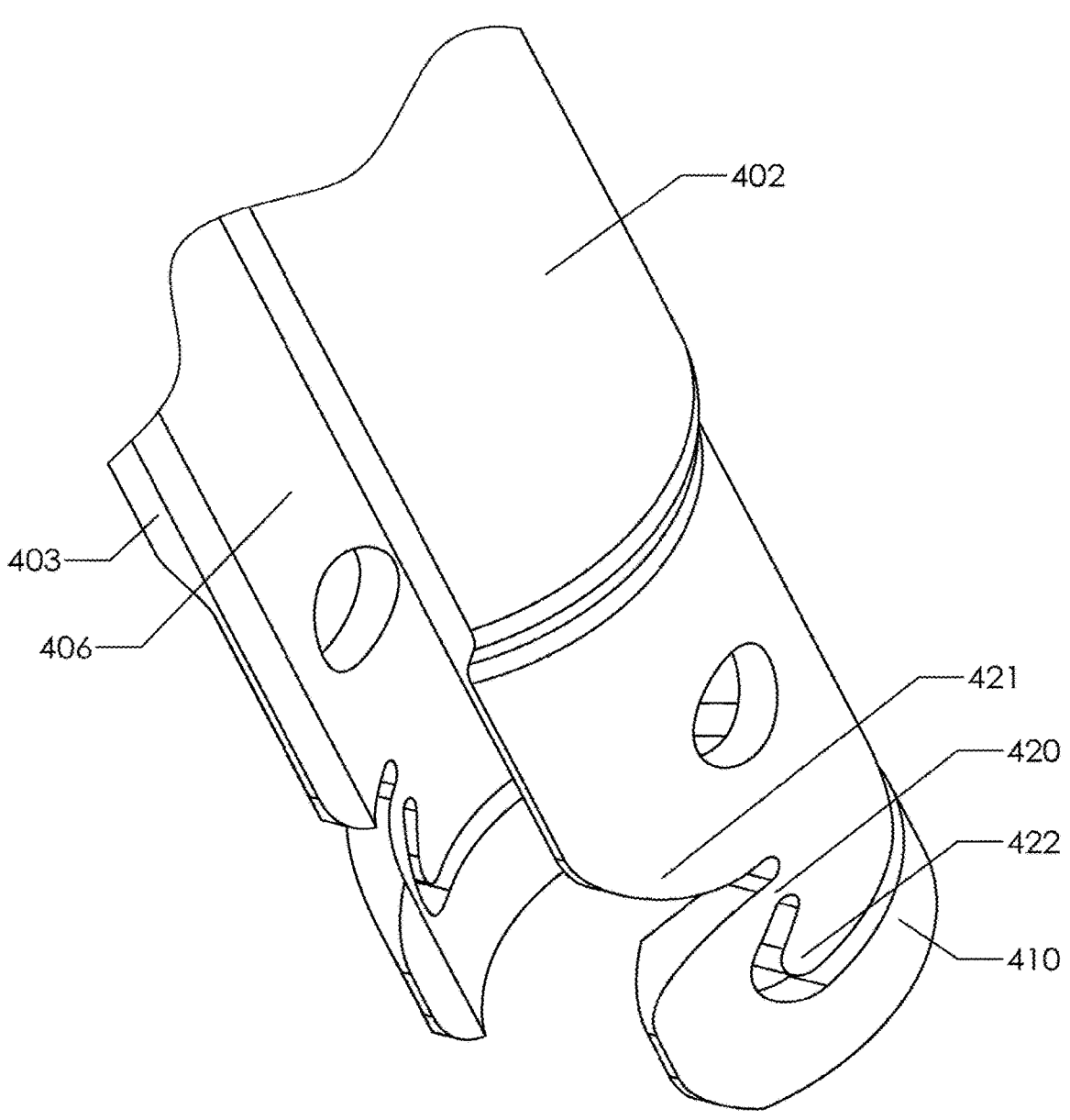
Figure 4E:
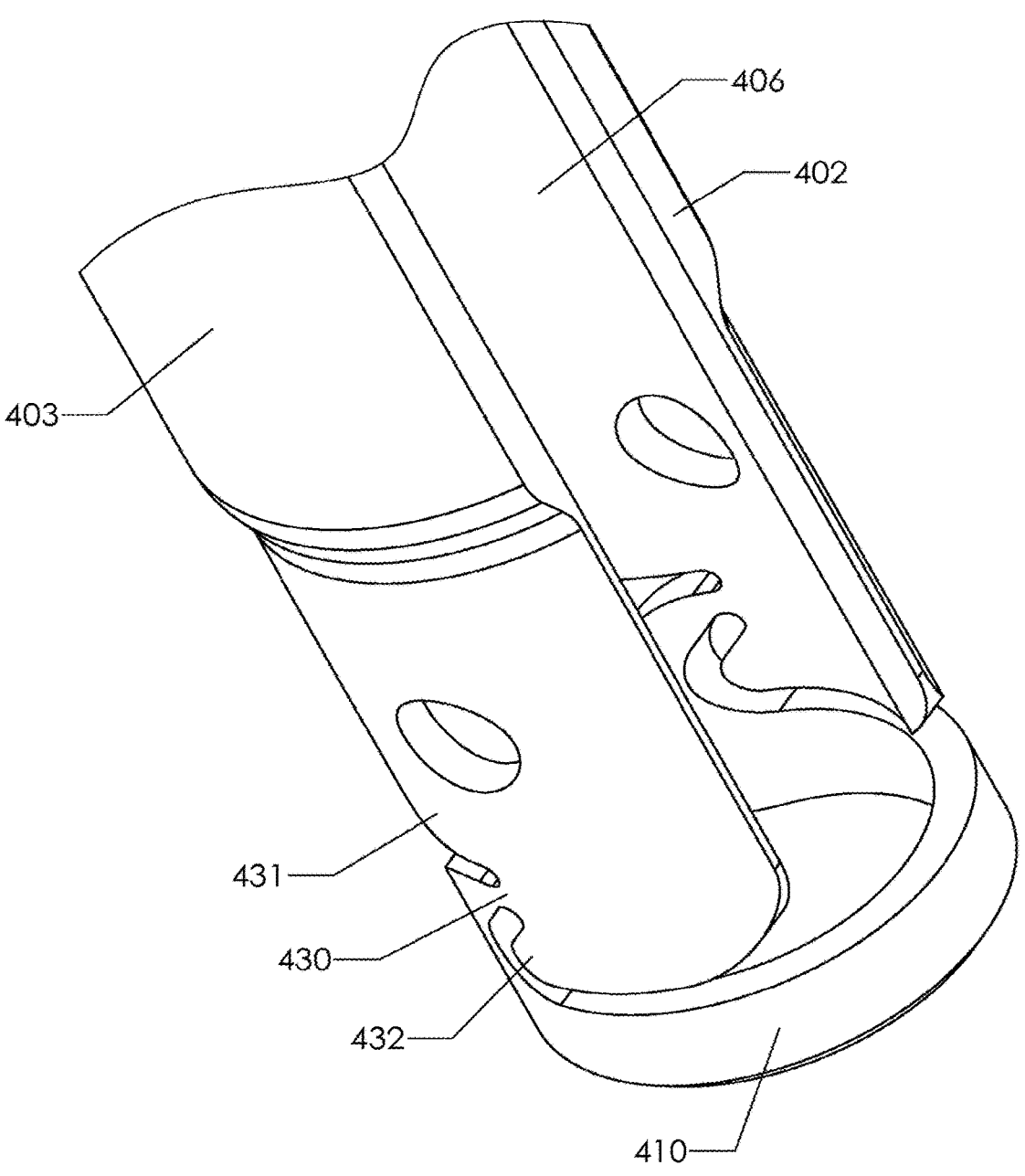

Alternative embodiments exist. FIG. 4A is similar to FIG. 2C but does not include tabs corresponding to tabs 240, 241. FIG. 4A includes screw 401 and link member 410 coupling proximal ends of sleeves 402, 403 to one another about window 406 (and another window, not shown, analogous to window 205). As with FIG. 2C, a distal recessed ring 408 is present for separating sleeves 402, 403 from saddle 407. Forgoing tabs corresponding to tabs 240, 241 may provide the physician with greater access to windows 406 (and unseen window analogous to window 205) for access to screw 401, tissue, and the like. As with FIG. 2C, elements 421, 422 (FIG. 4D) serve to protect a sharp edge at failure area 420 once linking ring 410 has been removed. As with FIG. 2C, elements 431, 432 (FIG. 4E) serve to protect a sharp edge at failure area 430 once linking ring 410 has been removed.

Still other alternative embodiments exist. The sleeves may be longer or shorter than 5.75". Other embodiments of sleeves may be 3, 4, 5, 6, 7, 8, 9 or more inches in length. Embodiments also come in a variety of widths. Furthermore, an embodiment shows two points of attachment (see 220, 230 of FIG. 2C) and two arms but other embodiments may include more arms (e.g., 3, 4, 5 arms) and/or more areas of coupling in the proximal end. For example, for a 3 arm embodiment the proximal ring may have 3 contact points (one for each arm). Also, fewer areas of coupling are possible.

Embodiments described herein do not necessarily include an exhaustive listing of every component that may be included in a system. For example, various spacers, lock nuts, and the like may be used with the system although not specifically described herein.

Various embodiments provide a system where tulip arms may be separated from one another via a simple rotation of a coupling member until that coupling member fatigues and fails. An embodiment includes a void for receiving a tool to allow the tool to securely attach to the ring and, while still in the void, cause the ring to pivot, fail, and separate from the tulip arms (but other embodiments, such as that of FIG. 4C require no void because tabs 240, 241 are not present and window 406 provides ample space to access and secure element 410). The rotation force (torque) is beyond minimal (so the physician does not accidentally separate the ring from the arms) but is still less than overly restrictive due to, for example, the moment arm that extends along the ring (e.g., dimension 261 of FIG. 2J) to the thinned severance points where the ring couples to the arms. This makes for a far easier separation for the physician, and the designated failure points for the proximal ring allow for a consistent experience for the physician (e.g., the ring fails at the same two places most every time the systems are used).

In another embodiment a single failure point is possible. For example, an embodiment similar to FIG. 2C includes no proximal ring 210 but instead couples the two arms at a single point. Thus, instead of the separation shown in FIG. 2C, in an alternative embodiment that separation is instead a seam. The physician may simply compress the two arms towards one another (e.g., with forceps) causing the arms to each rotate away from the seam, fatigue the seam, cause the seam to fail, and therefore separate the arms from one another. In another embodiment, the physician may simply spread the arms away from each other, causing the arms to each rotate towards the seam, fatigue the seam, cause the seam to fail, and therefore separate the arms from one another.

An embodiment includes a method of using an extended sleeve system. An embodiment includes inserting a K-wire through a cannulated needle sheath. Once the guide wire is inserted and firmly docked, the targeting needle is removed. With the K-wire in place a series of dilators are placed over the wire to create a working portal. At this point, the inner dilators are removed, leaving the outer dilator behind for subsequent surgical steps. A cannulated pedicle tap can then be passed over the K-wire. Fluoroscopy may be used to verify the position of the tap in relation to the K-wire, making sure that the tap does not advance further than the wire. The physician may pass the screw inserter through an extender sleeve of the screw and into a hex head. With the screw construct properly connected to the screw inserter, the screw may be passed over the K-wire down to the pedicle. The screw is advanced under fluoroscopic guidance until the screw reaches the posterior wall of the vertebral body. At this point, the K-wire is removed and the screw is advanced until the polyaxial head of the screw sits snugly against the base of the facet joint. At this time, the screw inserter and dilator may be removed, leaving the screw with the extender sleeve still attached. The previous surgical steps may be repeated in order to place a second pedicle screw (and other screws if need be). Once both screws are in position, the extender sleeves are rotated so that the slots face one another (i.e., so that windows such as windows 205, 206). The rod measurement tool is lowered down the extender sleeves to measure for the rod length.

After selecting the appropriate length rod, the physician uses the rod holder to guide the linkage rod down the two extended tabs on the pedicle screws and into the base of each screw. The rod holder can be used to adjust the cephalad/caudad position of the rod within the screws. After the linkage rod connects the screws the sleeves may be removed by removing element 210 (FIG. 2C) and then sleeves 202, 203.

Figure 5A:
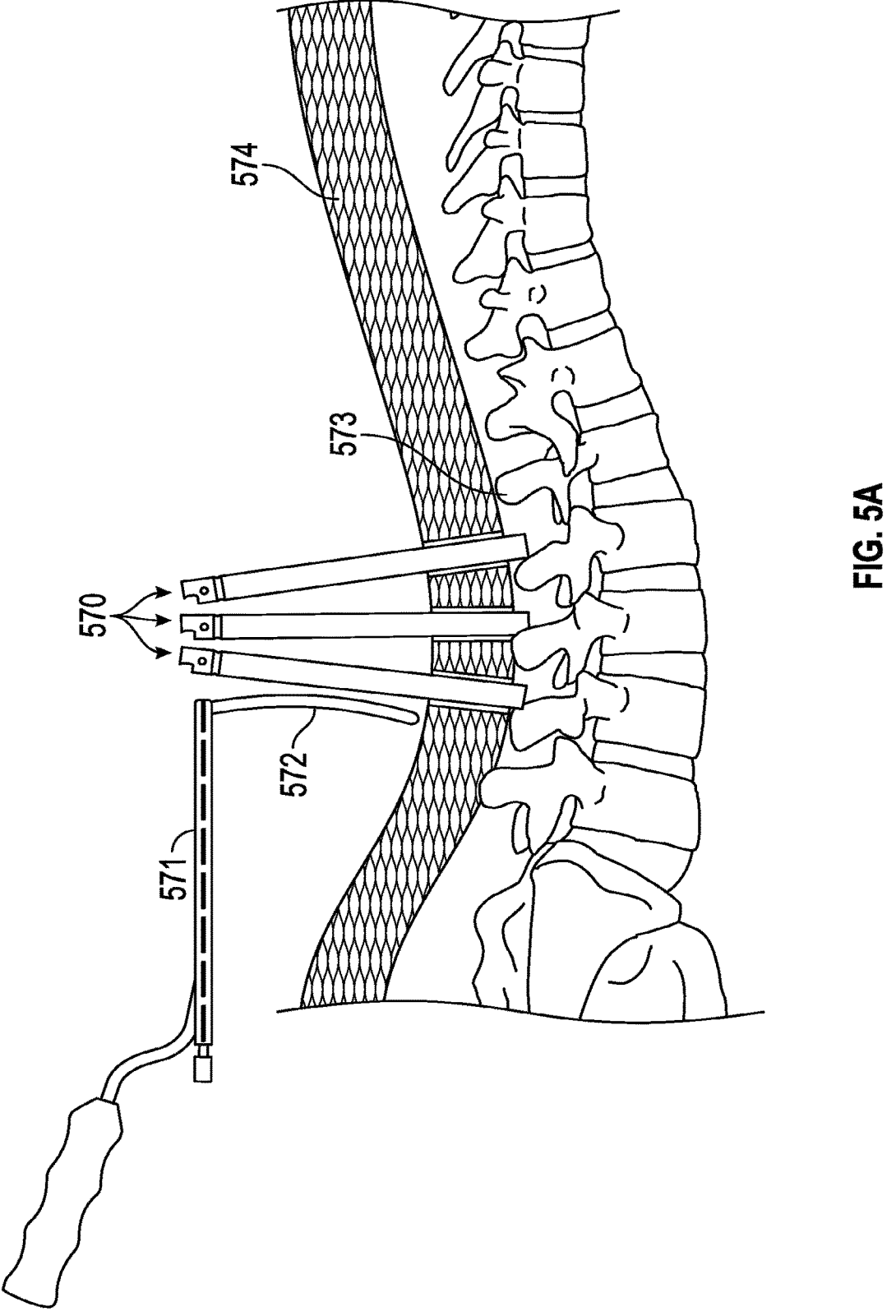
FIGS. 5A, 5B, 5C depict a method of implanting an embodiment of the invention.
Figure 5B:
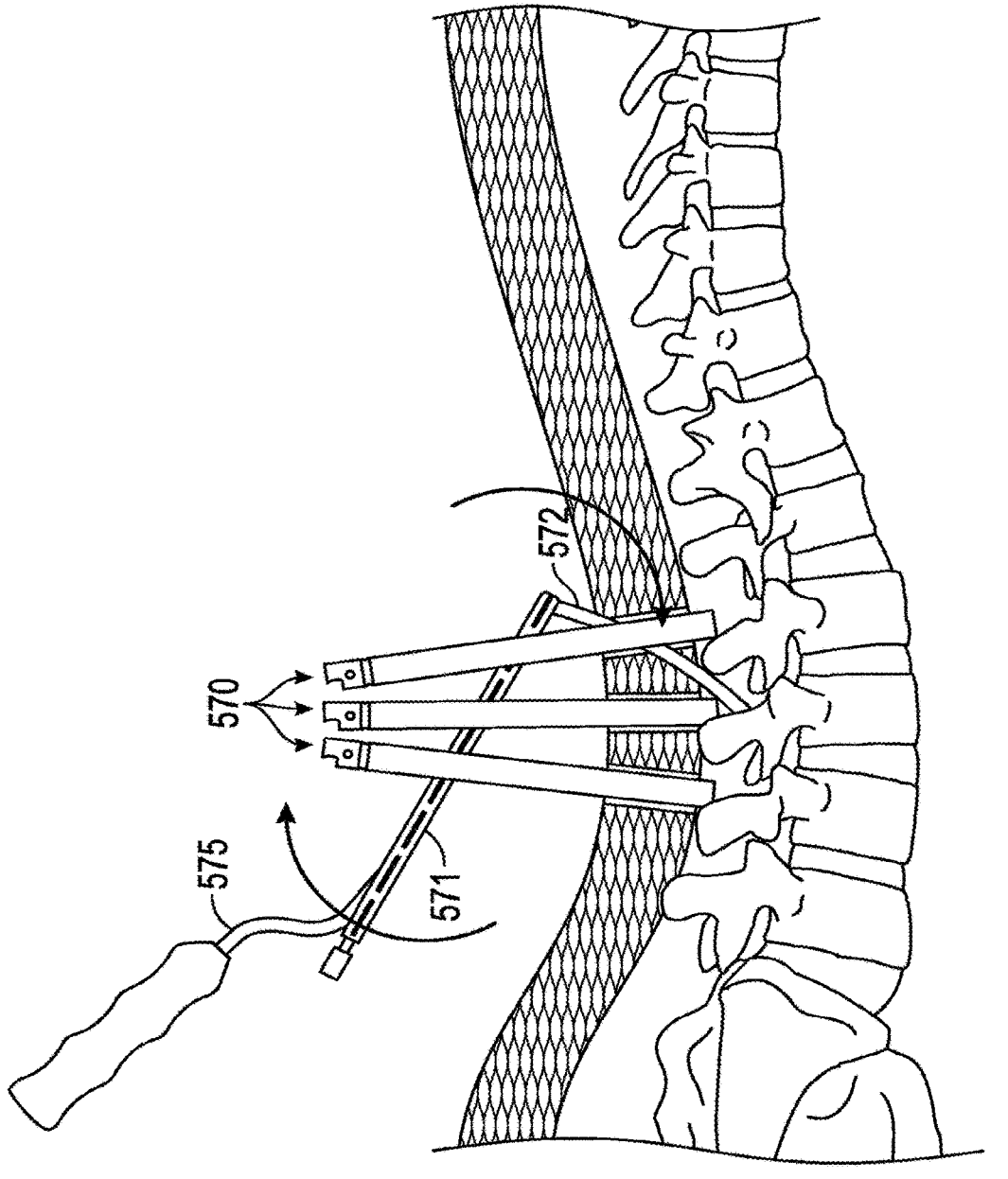
Figure 5C:
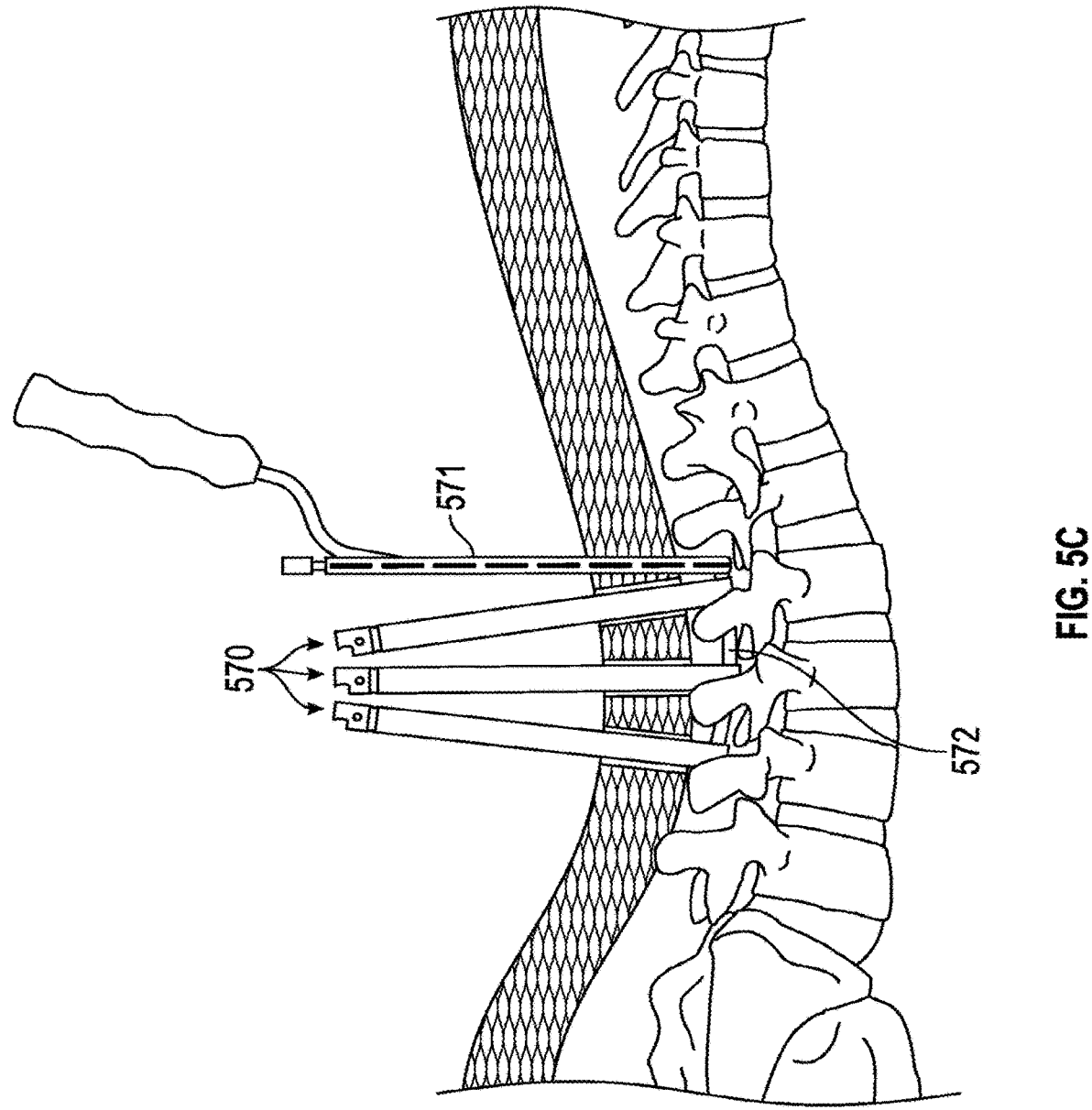

FIGS. 5A, 5B, 5C depict a method of implanting an embodiment of the invention. FIG. 5A depicts three tulip structures 570 with protective proximal rings (e.g., ring 210 from FIG. 2C) already removed. The tulip structures 570 are all passing through tissue 574 and contacting portions of spine 573. Screws are deployed into the spine and are located (but not shown) at the distal ends of tulip structures 570. In FIG. 5B the physician has passed the rod 572 and inserter assembly 571 through the towers (i.e., tulips 570). The physician has seated the distal tip of the rod 572 on to the saddle of a tulip to begin percutaneous tunneling through tissue 574. FIG. 5B shows the physician accessing the channels (e.g., spaces formed by windows 205, 206) between sleeves (e.g., 202, 203) for all three of the tulip structures. More specifically, the physician tunnels the rod through each tulip, by rotating the shaft and handle of the inserter 571 through each tower. This helps align and tunnel the rod through tissue and the towers. FIG. 5C shows the physician using a placement tool 571 (coupled to handle 575) to implant a linkage rod 572 (that will link three different pedicle screws) into its final position. Set screws (not shown) may then be placed down the tulips and over the rod 572 to help stabilize the spine (or any other bone portions, such as separate pieces of a femur in other embodiments).

Figure 6:
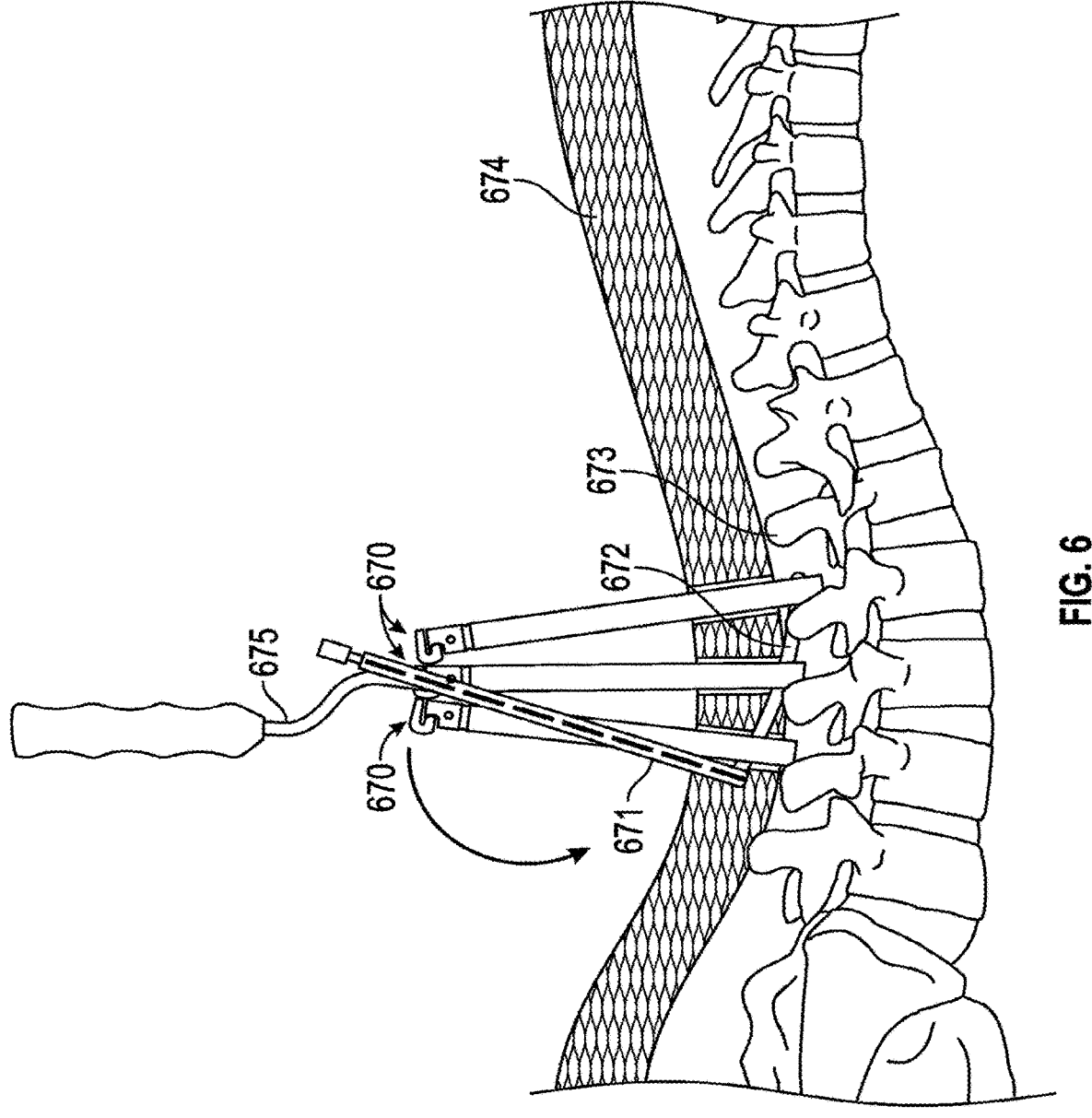
FIG. 6 depicts a method of implanting an embodiment of the invention.

FIG. 6 depicts a method of implanting an embodiment of the invention. FIG. 6 depicts three tulip structures 670 with protective proximal rings (e.g., ring 210 from FIG. 2C) still present. The physician passes the tip of the rod to the bottom of the tulip and then tunnels the rod through the tissue from tower to tower. The tulip structures 670 are all passing through tissue 674 and contacting portions of spine 673. Screws are deployed into the spine and are located (but not shown) at the distal ends of tulip structures 670. The physician accesses the channels (e.g., spaces formed by windows 205, 206) between sleeves (e.g., 202, 203) for all three of the tulip structures. The physician uses a placement tool 671 (coupled to handle 675) to implant a linkage rod 672 that will link three different pedicle screws. Set screws (not shown) may then be placed down the tulips and over the rod 672 to help stabilize the spine (or any other bone portions, such as separate pieces of a femur in other embodiments). In this embodiment the physician may have preferred to implant the rod 672 while the proximal rings are still intact because the proximal rings (e.g., 210) maintain stability of the sleeves and keep the sleeves from prematurely fracturing about distal recesses (e.g., 208) adjacent a saddle structure (e.g., 207). The physician may locate the placement device 670 adjacent tulips 670 in order to avoid tabs such as tabs 240, 241 of FIG. 2C.

Figure 7A:
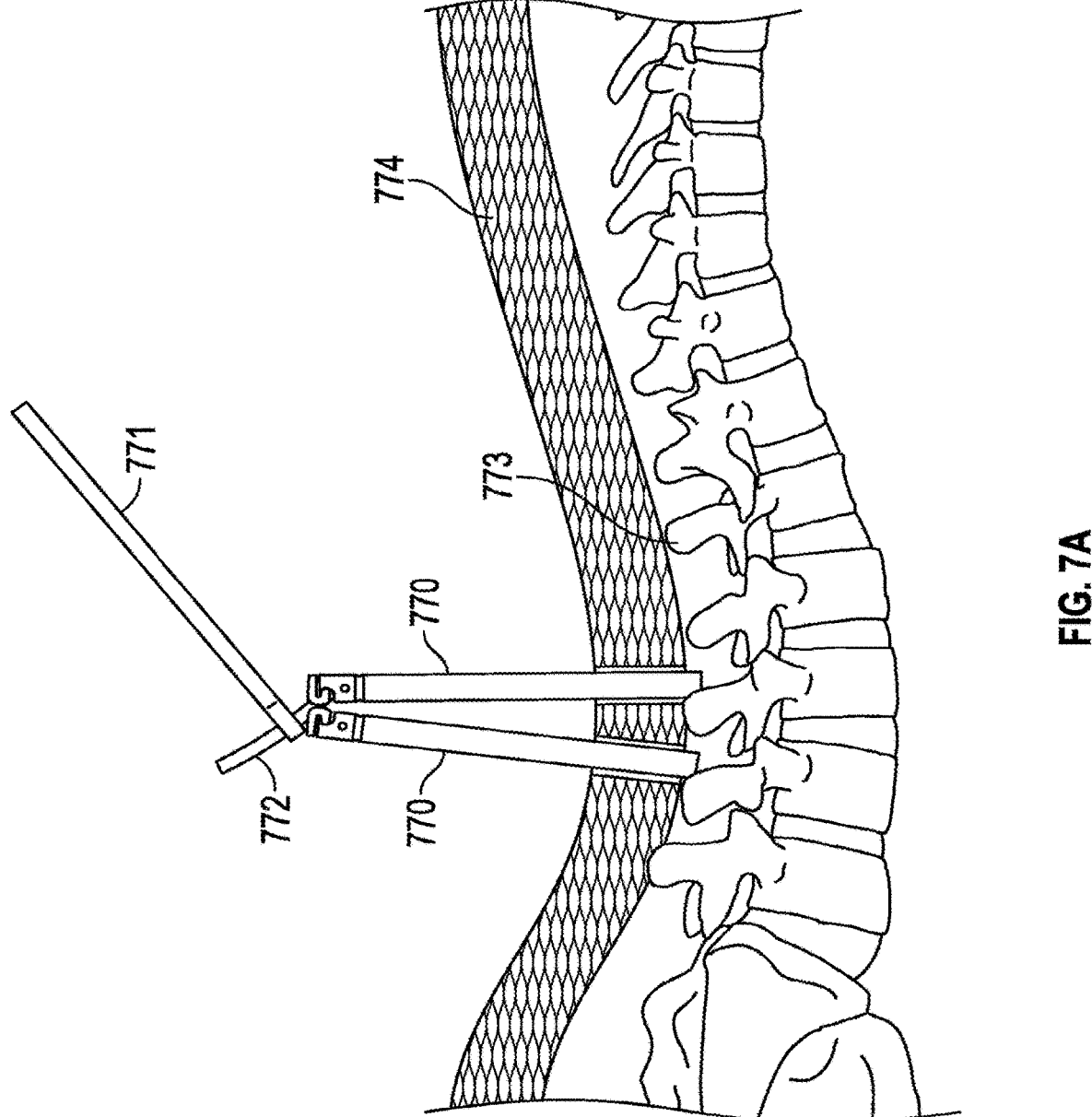
FIGS. 7A, 7B, 7C depict a method of implanting an embodiment of the invention.
Figure 7B:
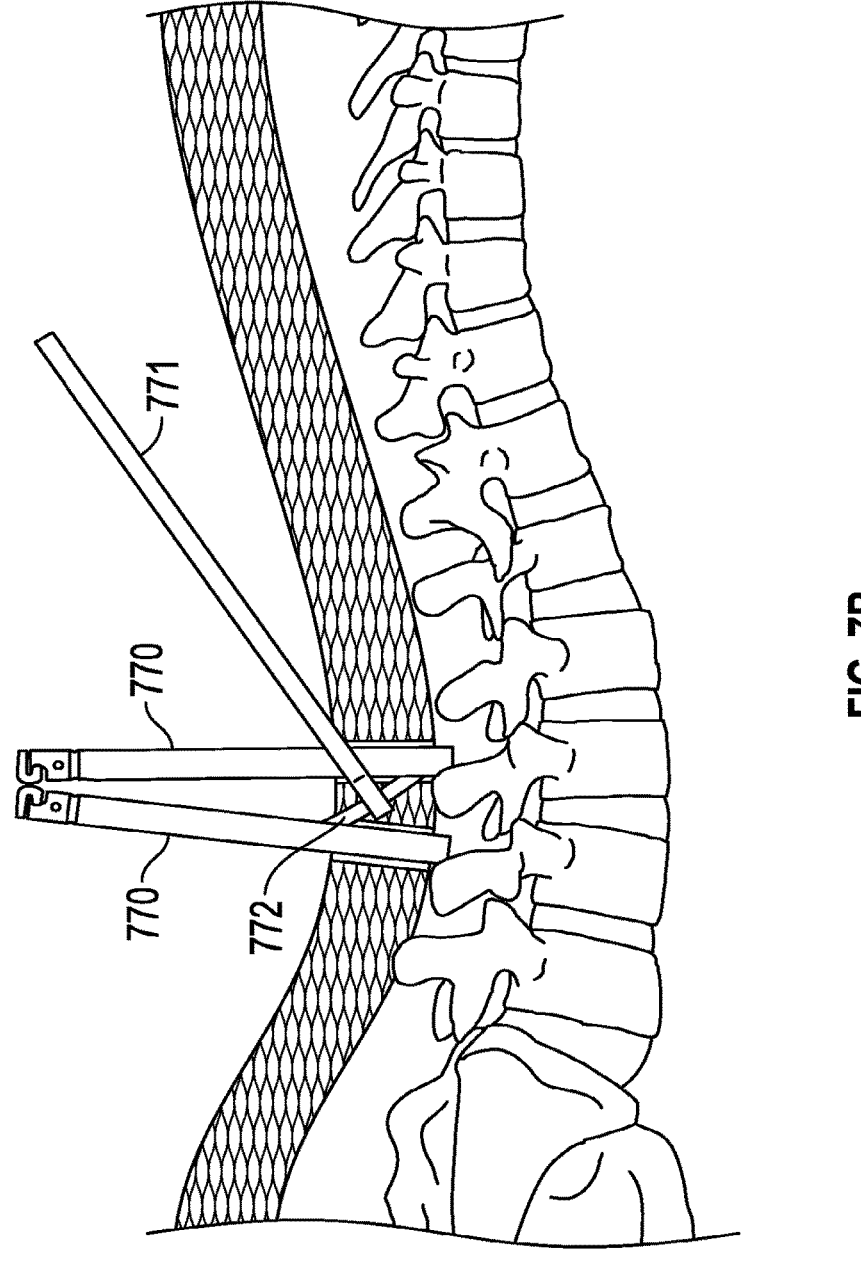
Figure 7C:
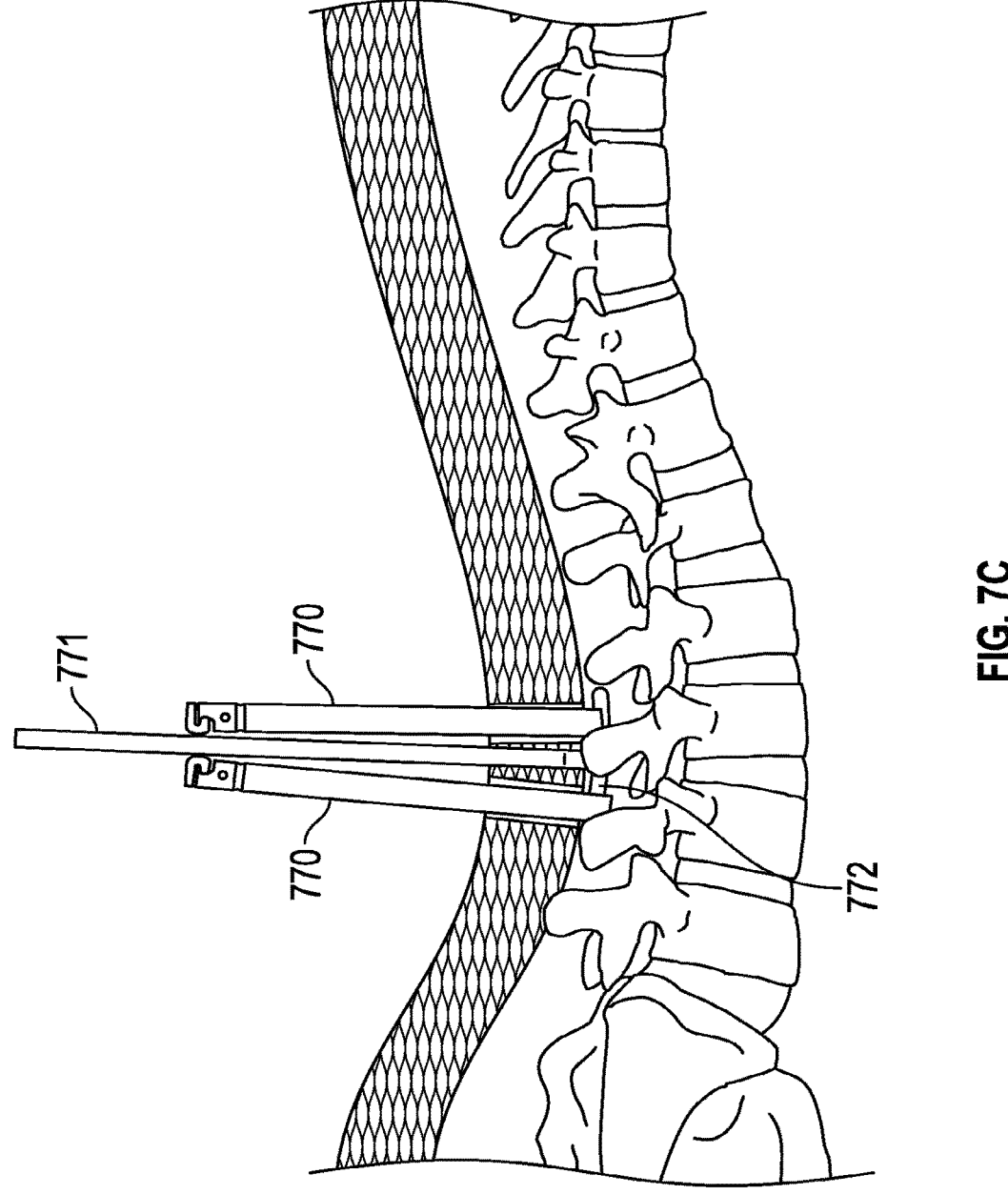

FIGS. 7A, 7B, 7C depict a method of implanting an embodiment of the invention. FIG. 7A depicts tulip structures 770 with protective proximal rings (e.g., ring 210 from FIG. 2C) still present. Specifically, the physician has inserted the rod into the first tower. Note how the towers are rotated 180 degrees from one another to allow the greatest access to the channels of the tulips (i.e., the "closed" portions of the rings 210 are located "outermost" and the "open" portions of the rings 210 are located adjacent one another). In this embodiment the physician may have preferred to implant the rod 772 while the proximal rings are still intact because the proximal rings (e.g., 210) maintain stability of the sleeves and keep the sleeves from prematurely fracturing about distal recess (e.g., 208) adjacent a saddle structure (e.g., 207). The tulip structures 770 are all passing through tissue 774 and contacting portions of spine 773. Screws are deployed into the spine and are located (but not shown) at the distal ends of tulip structures 770. FIG. 7B shows the physician accessing the channels (e.g., spaces formed by windows 205, 206) between sleeves (e.g., 202, 203) for the tulip structures. FIG. 7C shows the physician using a placement tool 771 to implant a linkage rod 772 that will link pedicle screws. Set screws (not shown) may then be placed down the tulips and over the rod 772 to help stabilize the spine (or any other bone portions, such as separate pieces of a femur in other embodiments). The physician may locate the placement device 770 within channels of tulips 770 easily using an embodiment, such as that of FIG. 4A, which does not include tabs such as tabs 240, 241 of FIG. 2C. In other words, without tabs 240, 241 the tool 771 and rod 772 can easily passed within channels of the tulips.

Materials for embodiments of the tulips may include, for example, cobalt alloys (e.g., cobalt chromium), titanium alloys (e.g., nickel titanium alloy (Nitinol)), commercially pure titanium, Ti 6Al-4V Eli, polyetheretherketone (PEEK), stainless steel, ceramics (e.g., aluminum oxide, zirconia, calcium phosphates), polymers (e.g., silicones, poly (ethylene), poly (vinyl chloride), polyurethanes, polylactides), natural polymers (e.g., collagen, gelatin, elastin, silk, polysaccharide, hydrogels), and the like.

An embodiment includes an orthopedic implant system comprising: a tulip including (a) an orifice at a distal end portion of the tulip to couple to an anchor element, (b) an open slot to receive a linkage, (c) first and second side walls that collectively define at least a portion of the open slot, and (d) a ring that couples the first side wall to the second side wall at a proximal end portion of the tulip; wherein the ring couples to the first side wall at a thinned first proximal fulcrum and to the second side wall at a thinned second proximal fulcrum and the ring pivots about the first and second proximal fulcrums when the ring is forced proximally; wherein the first side wall includes a first thinned portion forming a first distal fulcrum about which the first side wall rotates after the ring is removed from the tulip but not before the ring is removed from the tulip; wherein the second side wall includes a second thinned portion forming a second distal fulcrum about which the second side wall rotates after the ring is removed from the tulip but not before the ring is removed from the tulip; wherein the first side wall includes a first sidewall projection that projects past the first proximal fulcrum and the second side wall includes a second sidewall projection that projects past the second proximal fulcrum. A fulcrum includes the point on which a lever rests or is supported and on which the lever pivots.

An embodiment includes an orthopedic implant system comprising: a tulip including (a) an orifice at a distal end portion of the tulip to couple to an anchor element, (b) an open slot to receive a linkage, (c) first and second side walls that collectively define at least a portion of the open slot, and (d) a ring that couples the first side wall to the second side wall at a proximal end portion of the tulip; wherein the ring couples to the first side wall at a thinned first proximal fulcrum and to the second side wall at a thinned second proximal fulcrum and the ring pivots about the first and second proximal fulcrums when the ring is forced proximally; wherein the first side wall includes a first thinned portion forming a first distal fulcrum about which the first side wall rotates after the ring is removed from the tulip; wherein the second side wall includes a second thinned portion forming a second distal fulcrum about which the second side wall rotates after the ring is removed from the tulip; wherein the first side wall includes a first sidewall projection that projects past the first proximal fulcrum and the second side wall includes a second sidewall projection that projects past the second proximal fulcrum. A fulcrum includes the point on which a lever rests or is supported and on which the lever pivots.

An embodiment includes wherein the first side wall includes an additional first sidewall projection that projects past the first proximal fulcrum and the second side wall includes an additional second sidewall projection that projects past the second proximal fulcrum.

An embodiment includes wherein the first proximal fulcrum is proximal to the first sidewall projection and distal to the additional first sidewall projection.

An embodiment includes wherein the ring includes a midpoint and the first and second sidewalls form a void directly distal to the midpoint.

An embodiment includes wherein the void is entirely collinear with the first and second sidewalls.

An embodiment includes wherein the void includes a sidewall portion that is non-collinear with either of the first and second sidewalls.

An embodiment includes wherein a void is located directly between a proximal most portion of the first and second sidewalls and a distal portion of the ring such that an axis, parallel to a major axis of the system, intersects the ring and one of the first and second sidewalls.

An embodiment includes wherein the first sidewall includes a first axis parallel to a long axis of the tulip and the first axis intersects the first sidewall projection but not the first or second proximal fulcrums.

An embodiment includes wherein the first side wall includes an additional first sidewall projection that projects past the first sidewall projection and the second side wall includes an additional second sidewall projection that projects past the second sidewall projection.

An embodiment includes wherein the additional first sidewall projection is proximal to the first sidewall projection.

An embodiment includes wherein the ring is monolithic with the first and second sidewalls.

An embodiment includes wherein portions of the first and second sidewalls are threaded proximal to the first and second thinned portions.

An embodiment includes wherein the first and second thinned portions are recessed inwardly from exterior walls of the first and second side walls.

An embodiment includes wherein an exterior wall of the ring is collinear with at least a portion of an exterior wall of the first sidewall.

An embodiment includes wherein an exterior wall of the first proximal fulcrum extends radially no further than an exterior wall of the first sidewall projection.

An embodiment includes wherein the ring includes a midpoint and the first and second proximal fulcrums are equidistant from the midpoint.

An embodiment includes wherein the first and second proximal fulcrums each respectively project away from main portions of the first and second sidewalls and voids are included immediately proximal and distal to each of the first and second proximal fulcrums.

An embodiment includes wherein a maximum diameter of the first proximal fulcrum is less than 1.0 mm.

An embodiment includes wherein the first proximal fulcrum is configured to fail when the ring is forced proximally.

An embodiment includes wherein the first and second sidewall projections are rounded.

An embodiment includes an orthopedic implant system comprising: a conduit including (a) an orifice at a distal end portion of the conduit to couple to an anchor element, (b) an open slot to receive a linkage, (c) first and second side walls, disposed parallel to a long axis of the conduit, that collectively define at least a portion of the open slot, and (d) a lever, disposed parallel to a short axis of the conduit, that couples the first side wall to the second side wall at a proximal end portion of the conduit; wherein the lever couples to the first side wall at a first proximal fulcrum and to the second side wall at a second proximal fulcrum and the lever pivots about the first and second proximal fulcrums when the lever is forced proximally; wherein the first side wall includes a first sidewall projection that projects past the first proximal fulcrum and the second side wall includes a second sidewall projection that projects past the second proximal fulcrum.

An embodiment includes wherein the first side wall includes an additional first sidewall projection that projects past the first proximal fulcrum and the second side wall includes an additional second sidewall projection that projects past the second proximal fulcrum.

An embodiment includes wherein the first proximal fulcrum is proximal to the first sidewall projection and distal to the additional first sidewall projection.

An embodiment includes wherein the first side wall includes an additional first sidewall projection that projects past the first sidewall projection and the second side wall includes an additional second sidewall projection that projects past the second sidewall projection.

An embodiment includes wherein the ring includes a midpoint and the first and second proximal fulcrums are equidistant from the midpoint.

An orthopedic implant system comprising: a conduit including (a) an orifice at a distal end portion of the conduit to couple to an anchor element, (b) an open slot to receive a linkage, (c) first and second side walls, disposed along a long axis of the conduit, that collectively define at least a portion of the open slot, and (d) a lever, disposed along a short axis of the conduit, that couples the first side wall to the second side wall at a proximal end portion of the conduit; wherein the lever couples to the first side wall at a first proximal fulcrum and to the second side wall at a second proximal fulcrum and the lever pivots about the first and second proximal fulcrums when the lever is forced proximally; wherein the first side wall includes a first sidewall projection that projects past the first proximal fulcrum and the second side wall includes a second sidewall projection that projects past the second proximal fulcrum. In such an embodiment "along" may be mean "parallel" but in other embodiments that is not necessarily the case.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method comprising:

inserting a wire through a cannulated sheath;

placing a dilator over the wire, the dilator forming a working portal;

placing a screw over the wire and within the dilator, wherein: (a) the screw is included within an orifice of a conduit; (b) the conduit includes a lever and first and second side walls that define at least a portion of an open slot; (c) the lever couples to the first side wall at a first location and the second side wall at a second location; (d) a first void is between first and second projections of the first side wall; and (e) at least a portion of the first location is recessed from an exterior edge of the first side wall and at least a portion of the second location is recessed from an exterior edge of the second side wall;

placing a rod within the open slot and coupling the rod to a base of the screw; and fatiguing the lever to disconnect the lever from the conduit and then fatiguing the first and second sidewalls to decouple them from the screw.

2. The method of claim 1 comprising:

inserting an additional wire through an additional cannulated sheath;

placing an additional dilator over the additional wire, the additional dilator forming an additional working portal;

placing an additional screw over the additional wire and within the additional dilator, wherein: (a) the additional screw is included within an additional orifice of an additional conduit; (b) the additional conduit includes an additional lever and additional first and second side walls that define at least a portion of an additional open slot; (c) the additional lever couples to the additional first side wall at an additional first location and the additional second side wall at an additional second location; (d) an additional first void is between additional first and second projections of the additional first side wall; and (e) at least a portion of the additional first location is recessed from an exterior edge of the additional first side wall and at least a portion of the additional second location is recessed from an exterior edge of the additional second side wall;

placing the rod within the additional open slot and coupling the rod to a base of the additional screw; and fatiguing the additional lever to disconnect the additional lever from the additional conduit and then fatiguing the additional first and second sidewalls to decouple them from the additional screw.

3. The method of claim 1, wherein the lever is configured to fatigue, fail, and disconnect from at least one of the first sidewall at the first location, the second sidewall at the second location, or combinations thereof.

4. The method of claim 1, wherein the first void is immediately adjacent the first location.

5. The method of claim 1, wherein:

the lever is located in a proximal half of the conduit;

the open slot is located in the proximal half of the conduit and a distal half of the conduit.

6. The method of claim 5, wherein the first void directly interfaces the first location.

7. The method of claim 5, wherein:

a second void is immediately adjacent the second location;

the second side wall includes another first projection and another second projection;

the second void is between the another first projection and the another second projection.

8. The method of claim 1, wherein the lever includes a band and the band is substantially included in a plane.

9. The method of claim 8, wherein the band is arcuate and extends more than 180 degrees in the plane.

10. The method of claim 8, wherein the lever includes a midpoint and the first and second locations are equidistant from the midpoint.

11. The method of claim 1, wherein:

the first location has a maximum thickness measured orthogonal to a long axis of the conduit;

the first sidewall has an additional maximum thickness measured orthogonal to the long axis of the conduit;

the additional maximum thickness is thicker than the maximum thickness.

12. The method of claim 1, wherein the lever is configured to pivot about the first location in response to rotation of the lever.

13. The method of claim 12, wherein the lever is monolithic with the first and second sidewalls.

14. The method of claim 1, wherein the lever, the first side wall, and the second side wall are all included in a single contiguous piece of material.

15. The method of claim 1, wherein:

an exterior portion of the lever extends a first distance measured orthogonal to a long axis of the conduit;

an exterior portion of the first sidewall extends a second distance measured orthogonal to the long axis of the conduit;

the first distance is equal to the second distance.

16. The method of claim 1, wherein the first void directly interfaces at least one of the first or second projections.

17. The method of claim 1, wherein:

a second void is immediately adjacent the second location;

a third void is located directly between a proximal most portion of the first sidewall and a distal portion of the lever such that an axis intersects the lever, the third void, and one of the first and second sidewalls;

the axis is parallel to a long axis of the conduit.

18. The method of claim 1, wherein the first projection is proximal to at least a distal-most portion of the first location.

19. The method of claim 18, wherein:

the first location is a fulcrum;

the lever is configured to pivot about the fulcrum in response to the lever being rotated.

20. The method of claim 1, wherein:

the first location is a fulcrum;

the lever is configured to pivot about the fulcrum in response to the lever being rotated.

* * * * *